United States Patent
Hochi et al.

(10) Patent No.: US 10,563,025 B2
(45) Date of Patent: Feb. 18, 2020

(54) POLYMER FILM, AND DISPERSION LIQUID AND AGGLOMERATE USING SAME

(71) Applicants: Toray Industries, Inc., Tokyo (JP); Nanotheta Co., Ltd., Tokyo (JP)

(72) Inventors: Motonori Hochi, Otsu (JP); Yuki Sekido, Otsu (JP); Ichiro Itagaki, Tokyo (JP); Toru Arakane, Tokyo (JP); Shinya Ohtsubo, Tokyo (JP); Shinji Takeoka, Tokyo (JP); Atsushi Murata, Tokyo (JP); Mao Fujii, Otsu (JP); Yuya Ishizuka, Saitama (JP); Shuichi Shoji, Tokorozawa (JP); Jun Mizuno, Kawagoe (JP); Takashi Kasahara, Tokyo (JP)

(73) Assignees: Toray Industries, Inc., Tokyo (JP); Nanotheta Co, Ltd., Tokyo (JP)

( * ) Notice: Subject to any disclaimer, the term of this patent is extended or adjusted under 35 U.S.C. 154(b) by 109 days.

(21) Appl. No.: 15/572,210

(22) PCT Filed: May 11, 2016

(86) PCT No.: PCT/JP2016/063946
§ 371 (c)(1),
(2) Date: Nov. 7, 2017

(87) PCT Pub. No.: WO2016/181977
PCT Pub. Date: Nov. 17, 2016

(65) Prior Publication Data
US 2018/0118905 A1    May 3, 2018

(30) Foreign Application Priority Data
May 11, 2015    (JP) .................. 2015-096305

(51) Int. Cl.
| | |
|---|---|
| A61K 8/04 | (2006.01) |
| A61K 8/81 | (2006.01) |
| A61K 8/85 | (2006.01) |
| A61K 8/86 | (2006.01) |
| A61L 15/22 | (2006.01) |
| C08J 5/18 | (2006.01) |
| A61L 31/00 | (2006.01) |
| A61L 15/24 | (2006.01) |
| A61L 15/26 | (2006.01) |
| A61L 31/04 | (2006.01) |
| A61L 31/06 | (2006.01) |
| A61Q 19/00 | (2006.01) |
| C08L 25/06 | (2006.01) |
| C08L 33/12 | (2006.01) |
| C08L 67/04 | (2006.01) |

(52) U.S. Cl.
CPC .............. *C08J 5/18* (2013.01); *A61K 8/04* (2013.01); *A61K 8/8117* (2013.01); *A61K 8/8152* (2013.01); *A61K 8/8176* (2013.01); *A61K 8/85* (2013.01); *A61K 8/86* (2013.01); *A61L 15/22* (2013.01); *A61L 15/225* (2013.01); *A61L 15/24* (2013.01); *A61L 15/26* (2013.01); *A61L 31/00* (2013.01); *A61L 31/04* (2013.01); *A61L 31/041* (2013.01); *A61L 31/048* (2013.01); *A61L 31/06* (2013.01); *A61Q 19/00* (2013.01); *C08L 25/06* (2013.01); *C08L 33/12* (2013.01); *C08L 67/04* (2013.01); *C08J 2325/06* (2013.01); *C08J 2333/12* (2013.01); *C08J 2367/04* (2013.01); *C08J 2467/04* (2013.01)

(58) Field of Classification Search
CPC .... C08J 5/18; A61K 8/04; C08L 25/06; C08L 33/12; C08L 67/04
See application file for complete search history.

(56) References Cited

FOREIGN PATENT DOCUMENTS

| | | |
|---|---|---|
| JP | 2-57263 A | 2/1990 |
| JP | 2001-192337 A | 7/2001 |
| JP | 2003-153999 A | 5/2003 |
| JP | 2004-065780 A | 3/2004 |
| JP | 2011-025013 A | 2/2011 |
| JP | 2012-187926 A | 10/2012 |
| WO | 2005/094915 A1 | 10/2005 |
| WO | 2008/050913 A1 | 5/2008 |
| WO | 2011/046226 A1 * | 4/2011 |

* cited by examiner

*Primary Examiner* — Alma Pipic
(74) *Attorney, Agent, or Firm* — DLA Piper LLP (US)

(57) ABSTRACT

A polymer film has an average film thickness $T_0$ along a straight line D passing through the center of gravity of a two-dimensional projection such that the area of the polymer film is maximized, satisfies equation (a), the average value L of distances l from the center of gravity to edges satisfies equation (b), the Young's modulus E satisfies equation (c), and the thickness deviation $\Delta$ defined by equation (d) satisfies equation (e); and a dispersion liquid and an agglomerate using the same. (a) 10 nm$\leq T_0 \leq$1000 nm, (b) 0.1 µm$\leq$L$\leq$500 µm, (c) 0.01 GPa$\leq$E$\leq$4.3 GPa, (d) $\Delta=1-T_1/T_2$, (e) $0.346E\times10^{-9}-1.499<\Delta<-0.073E\times10^{-9}+0.316$.

6 Claims, 16 Drawing Sheets

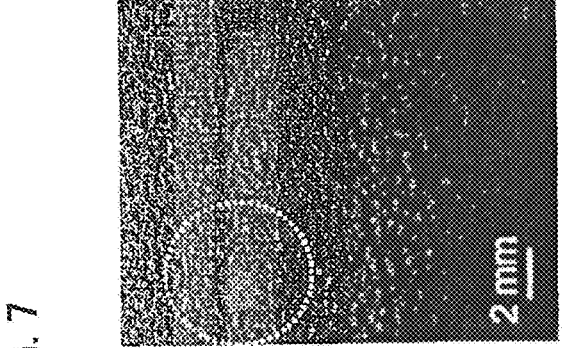
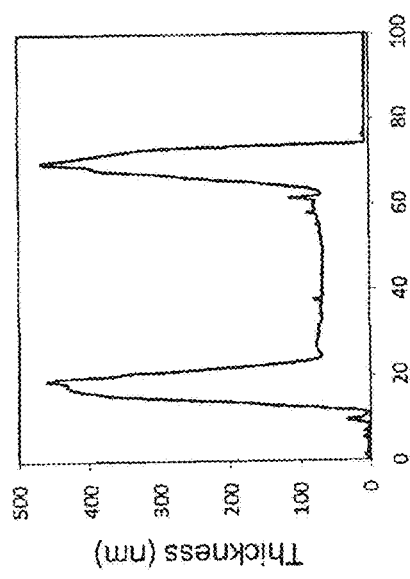
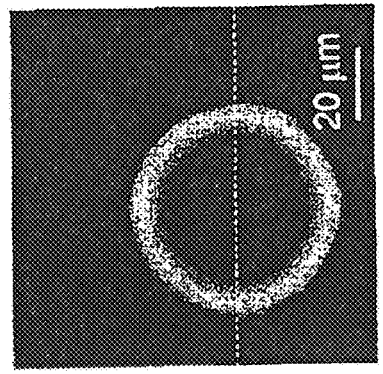
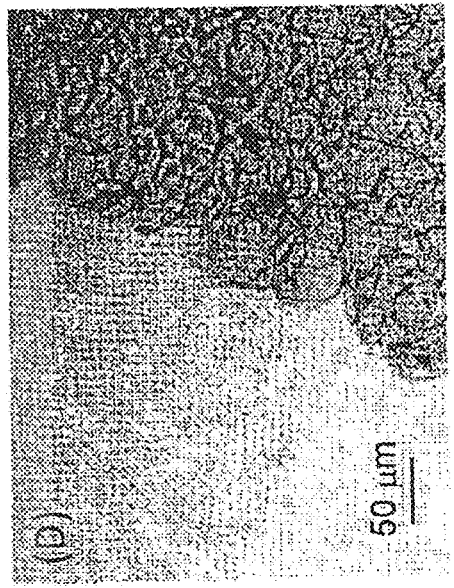
FIG. 7 (A)
FIG. 7 (B)
FIG. 7 (C)
FIG. 7 (D)

POLYMER FILM, AND DISPERSION LIQUID AND AGGLOMERATE USING SAME

TECHNICAL FIELD

This disclosure relates to a polymer film suitable for medical use such as hemostasis at surgical operation, wound-dressing films, adhesion-preventing films, percutaneous absorbing materials and the like and cosmetic materials, and a dispersion liquid and an agglomerate using the polymer film.

BACKGROUND

As one of complications after laparotomy surgery in abdominal surgery, gynecology and the like, there is an adhesion of organs. This may be caused in a wound healing process of surgery by reformation while tissues that essentially should not be in contact are brought into contact with each other, and this is known as adhesion. It is said that adhesion is caused at a high possibility in a laparotomy surgery, but many are asymptomatic. Although not frequent, adhesion may lead to pain or serious complications such as ileus or sterility.

Since once formed adhesions cannot be treated non-invasively, when having severe complications such as ileus, there is only surgical operation to peel off the adhesion site and, therefore, it is extremely important to firmly carry out a treatment of the wound site aimed for prevention of adhesion after initial surgery.

Conventionally, as a material having an adhesion-preventing effect, a method of using silicon, "Teflon (registered trademark)," polyurethane or the like as an adhesion-preventing material to physically separate organ tissues has been performed. However, because these materials are non-bioabsorbable materials, they remain on the surface of the biological tissue, and not only do they delay repair of the tissue, but also they cause infection and inflammation.

In recent years, to solve such problems, adhesion-preventing materials using natural polymers such as gelatin or collagen which can expect bioabsorbability are reported (for example, JP 2004-065780 A and JP 2001-192337 A). However, because gelatin and collagen have a problem in that it is difficult to remove a telopeptide part having an antigenicity and, further, there is a risk of infectious diseases derived from organisms such as prion contamination, it is better to avoid using to an organism. Moreover, there are many cases where a crosslinking agent added to obtain strength and control degradability is not preferred for use in an organism.

In a natural polymer, there is such a problem that it is low in strength though it is high in affinity with skin. Therefore, in a natural polymer, it has been necessary to ensure strength by a material crosslinked with a crosslinking agent or by use of a reinforcement material or by wrapping with a gauze. When a reinforcement material is used, because there are many cases where the structure becomes complicated, it is not practical.

Further, there is also a report on adhesion-preventing materials using polysaccharides such as trehalose and sodium alginate, which are low in risk of infections (for example, JP 2003-153999 A). However, since there is a problem that polysaccharide film materials cannot reliably cover the wound site because of rupture or the like due to lack of strength, they are low in practical use. Among polysaccharides, there is a report on adhesion-preventing materials using hyaluronic acid (for example, WO 2005/094915 A1). Since hyaluronic acid is high in water solubility, it absorbs moisture in the body and gels, but because the gel moves in the direction of gravity with time, there are problems that an effect cannot be obtained because sufficient ingredients do not remain in the affected area, and that bacteria proliferate in the gel pool accumulated by moving in the direction of gravity and may cause infection.

Furthermore, to strongly adhere the adhesion-preventing film to the organ and the like, although there are a method for using blood products and a method for using chemical substances, those methods include a problem that a high-quality management in viewpoint of safety is required and it is difficult to be handled.

In addition, as a method excellent in adherence with the affected part and can suppress movement in the direction of gravity, although a polymer structure in which a biodegradable resin layer of polylactic acid or the like and a water-soluble resin layer are laminated has been proposed, control of solubility of the water-soluble resin and handling property (stickiness) at the time of surgery was not sufficient (for example, JP 2012-187926 A).

Thus, although there are many reports relating to materials to prevent tissue adhesion, a material having a satisfactory performance as an adhesion-preventing material has not been obtained. Namely, a material, being hard to cause the above-described problems and capable of preventing adhesion until a tissue is recovered and maintaining a sufficient strength until the tissue is recovered, is required.

Especially in recent years, although laparoscopic surgery and endoscopic surgery are increasing to alleviate the physical burden of patients in surgical operations, conventional sheet-like adhesion-preventing materials are difficult to be passed through the inside of a tube (drain) placed in the horacic cavity and used for treatment of pneumothorax, pleural effusion, empyema and the like such as a trocar and, further, in a liquid adhesion inhibitor, there is a problem of poor coatability because it is poor in flowability.

It could therefore be helpful to provide a polymer film which is easy to handle and excellent in followability, coatability, adhesiveness and adherence to organ tissues, and a dispersion liquid and an agglomerate using the same.

SUMMARY

We thus provide:

[1] A polymer film characterized in that an average film thickness $T_0$ along a straight line D passing through a center of gravity of a two-dimensional projection such that the area of the polymer film is maximized, satisfies equation (a), an average value L of distances 1 from the center of gravity to edges in straight lines D passing through the center of gravity satisfies equation (b), a Young's modulus E satisfies equation (c), and a thickness deviation Δ defined by equation (d) satisfies equation (e):

$$10 \text{ nm} \leq T_0 \leq 1000 \text{ nm} \tag{a}$$

$$0.1 \text{ μm} \leq L \leq 500 \text{ μm} \tag{b}$$

$$0.01 \text{ GPa} \leq E \leq 4.3 \text{ GPa} \tag{c}$$

$$\Delta = 1 - T_1/T_2 \tag{d}$$

$$0.346E \times 10^{-9} - 1.499 < \Delta < -0.073E \times 10^{-9} + 0.316. \tag{e}$$

Here, $T_1$ and $T_2$ represent, in the straight line D passing through the center of gravity of the two-dimensional projection such that the area of the polymer film is maximized, $T_1$: an average film thickness of a region from ½ to 1 of the distance 1 from the center of gravity to the edge, and $T_2$: an average film thickness of a region from the center of gravity to ¼, and the straight line D passing through the center of gravity of the two-dimensional projection means the following $D_1$ to $D_4$:

(1) a minor axis passing through the center of gravity: $D_1$, (2) a major axis passing through the center of gravity: $D_2$, (3) straight lines passing through the center of gravity and bisecting a wide angle and a narrow angle formed by the minor axis and the major axis respectively: $D_3$, $D_4$.

When the minor axis and the major axis are the same or there are a plurality of them, two lines having the smallest difference between the wide angle and the narrow angle formed by the minor axis and the major axis are selected. Each average film thickness means an average value calculated using the four straight lines $D_1$ to $D_4$ selected according to the above.

[2] The polymer film according to [1], wherein a polymer constituting the polymer film is a homopolymer selected from a polyester-based resin, a polyether-based resin, a polymethacrylate-based resin, a polysaccharide and a polysaccharide ester, and/or, a copolymer containing at least one kind of polymer selected from a polyester-based resin, a polyether-based resin, a polymethacrylate-based resin, a polysaccharide and a polysaccharide ester.

[3] The polymer film according to [1] or [2], wherein the polymer film has at least one shape selected from the group consisting of a circle, an ellipse, an approximately circular shape, an approximately elliptical shape, an approximately polygonal shape and a ribbon-like shape.

[4] A dispersion liquid in which the polymer film according to any one of [1] to [3] is dispersed in a solution.

[5] A polymer film agglomerate using the polymer film according to any one of [1] to [3].

The polymer film has a fine flat shape generally called as a flake shape, a disk shape or the like, and by controlling the cross-sectional shape and Young's modulus thereof, when the polymer films overlap each other on the organ surface, the adhesive strength between the polymer films can be strengthened, and when applied with an external force, they are not collapsed and they can retain a stable shape as a polymer film agglomerate. Moreover, since the polymer film is a thin film, it is also excellent in followability and adherence to organs such as skin and internal organs.

Furthermore, the polymer film, and the dispersion liquid using powder, water or the like containing a plurality of the polymer films can easily pass through the inside of a tube such as a trocar (a tube placed in the thoracic cavity and used for treatment of pneumothorax, pleural effusion, empyema and the like), and it becomes possible to coat the organ surface over a wide range. Furthermore, because the size of the polymer film is very small and the film thickness is 1000 nm or less, by overlapping on the surface of these organs to form a film-like shape, excellent followability and adherence can also be achieved.

Because of such effects, the polymer film is optimal for medical applications such as wound dressing materials, adhesion-preventing films and the like, and as skin external materials such as skin care products, cosmetic materials and the like.

BRIEF DESCRIPTION OF THE DRAWINGS

FIGS. 7A-7E show a PDLLA film prepared by micro contact printing using a 2.0 mass % PLLA-4 PEG ethyl formate solution shown in Example 5. (A) shows an AFM image thereof, (B) is a cross-sectional view of a dotted line part in the AFM image, (C) is a diagram showing a self-supportability at a gas-liquid interface of an agglomerate of polymer film, (D) is an optical microscope image, and (E) is an SEM image when an arm model is coated with dispersion liquid for a polymer film.

is an optical microscope image, and (E) is an SEM image when an arm model is coated with dispersion liquid for a polymer film.

Figure 10A:
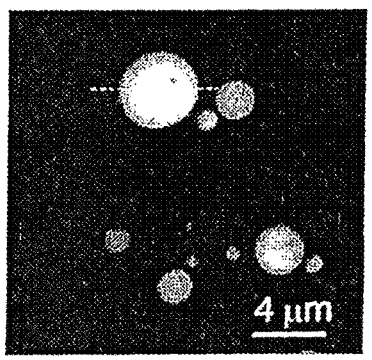
Figure 10B:
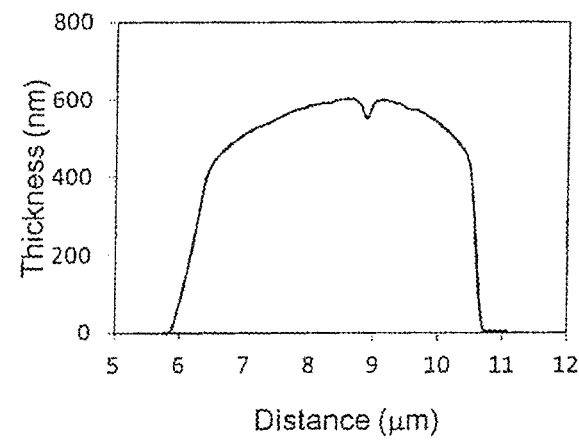

FIGS. 10A-10B show a PS film prepared by a phase separation film of 3.0 mass % PS:PVP=1:3 (mass ratio) shown in Comparative Example 1. (A) shows an AFM image thereof, and (B) is a cross-sectional view of a dotted line part in the AFM image.

Figure 11A:
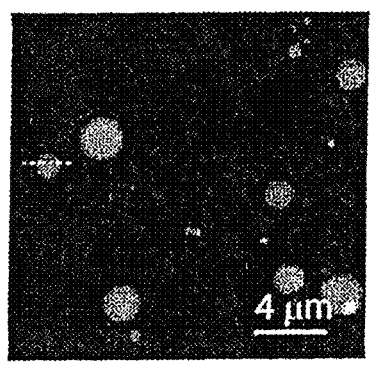
Figure 11B:
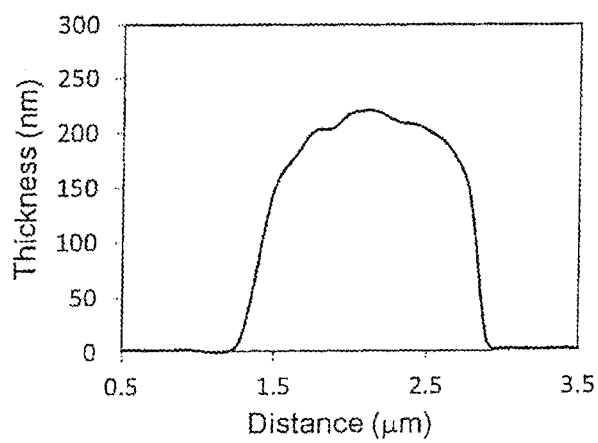

FIGS. 11A-11B show a PS film prepared by a phase separation film of 2.0 mass % PS:PVP=1:4 (mass ratio) shown in Comparative Example 2. (A) shows an AFM image thereof, and (B) is a cross-sectional view of a dotted line part in the AFM image.

Figure 12A:
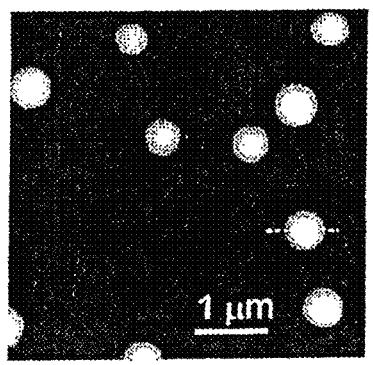
Figure 12B:
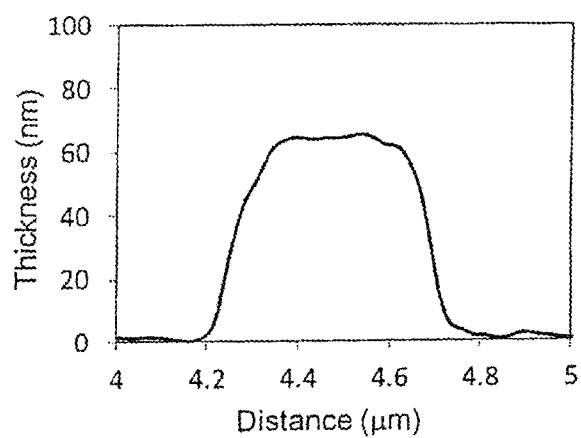

FIGS. 12A-12B show a PS film prepared by a phase separation film of 1.0 mass % PS:PVP=1:4 (mass ratio) shown in Comparative Example 3. (A) shows an AFM image thereof, and (B) is a cross-sectional view of a dotted line part in the AFM image.

Figure 13A:
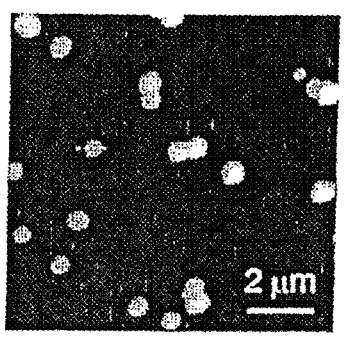
Figure 13B:
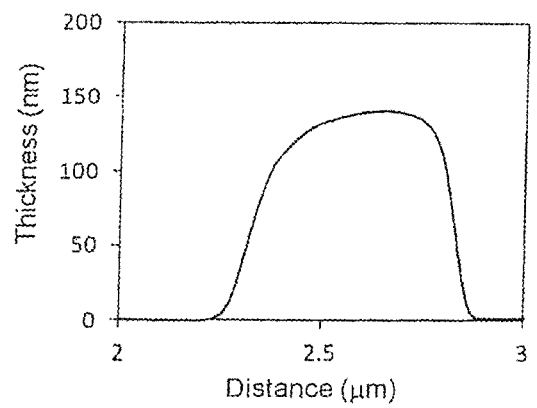

FIGS. 13A-13B show a PDLLA film prepared by a phase separation film of 2.0 mass % PDLLA:PVP-PVPAc=1:9 (mass ratio) shown in Comparative Example 4. (A) shows an AFM image thereof, and (B) is a cross-sectional view of a dotted line part in the AFM image.

Figure 14A:
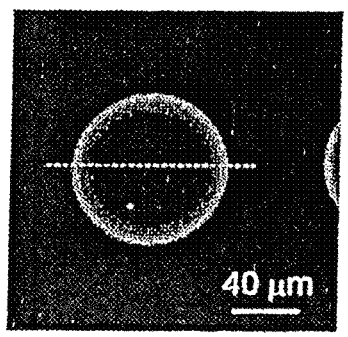
Figure 14B:
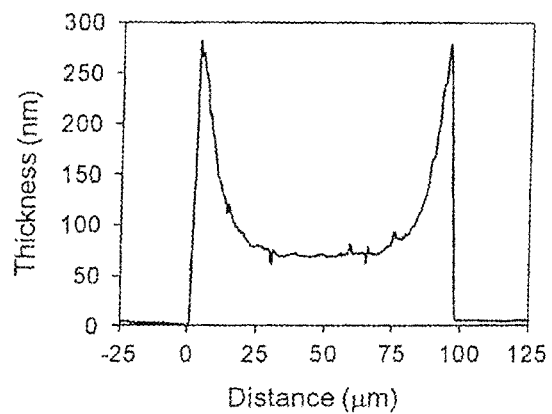

FIGS. 14A-14B show a PDLLA film prepared by micro contact printing using a 1.5 mass % PDLLA ethyl acetate solution shown in Comparative Example 5. (A) shows an AFM image thereof, and (B) is a cross-sectional view of a dotted line part in the AFM image.

Figure 15:
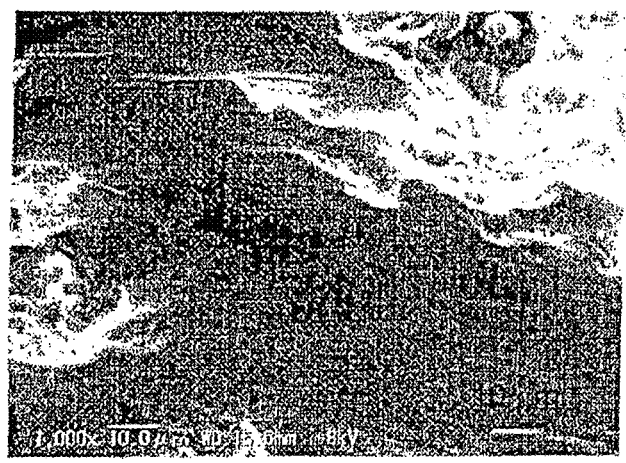

FIG. 15 shows an SEM image when an arm model is coated with a PDLLA film prepared by an ethyl acetate solution of 0.7 mass % PDLLA shown in Comparative Example 6.

Figure 16:
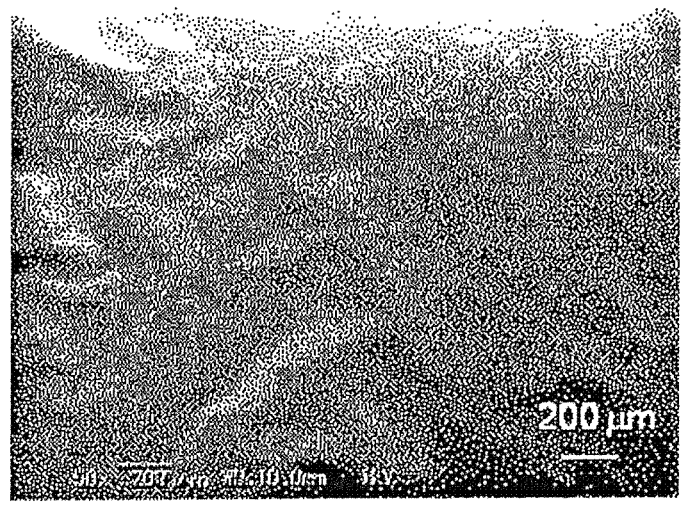

FIG. 16 shows an SEM image when an arm model is coated with a PDLLA film prepared by an ethyl acetate solution of 7.5 mass % PDLLA shown in Comparative Example 7.

Figure 17:
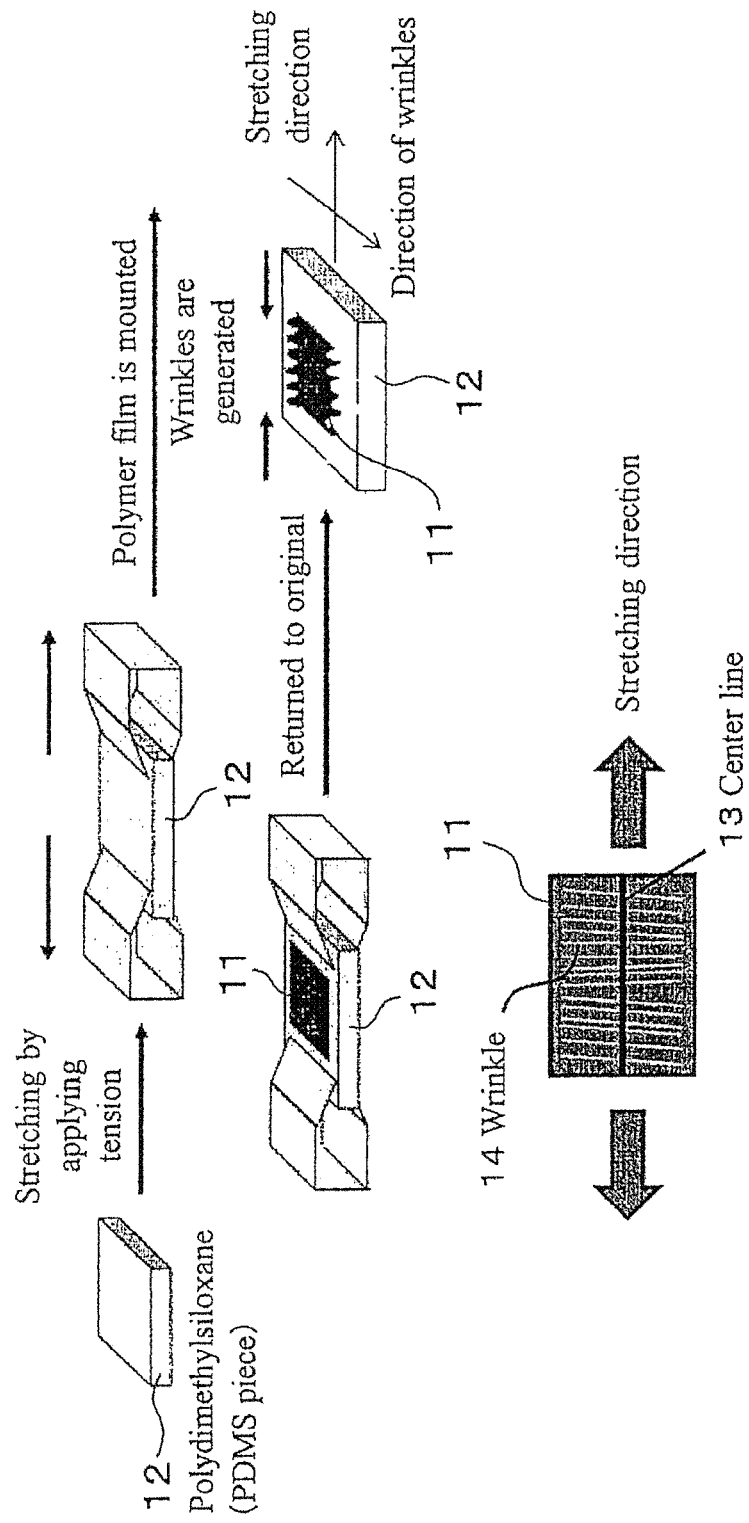

FIG. 17 is a schematic diagram showing a stretching direction and a wrinkle direction in an SIEBIMM method.

Figure 18:
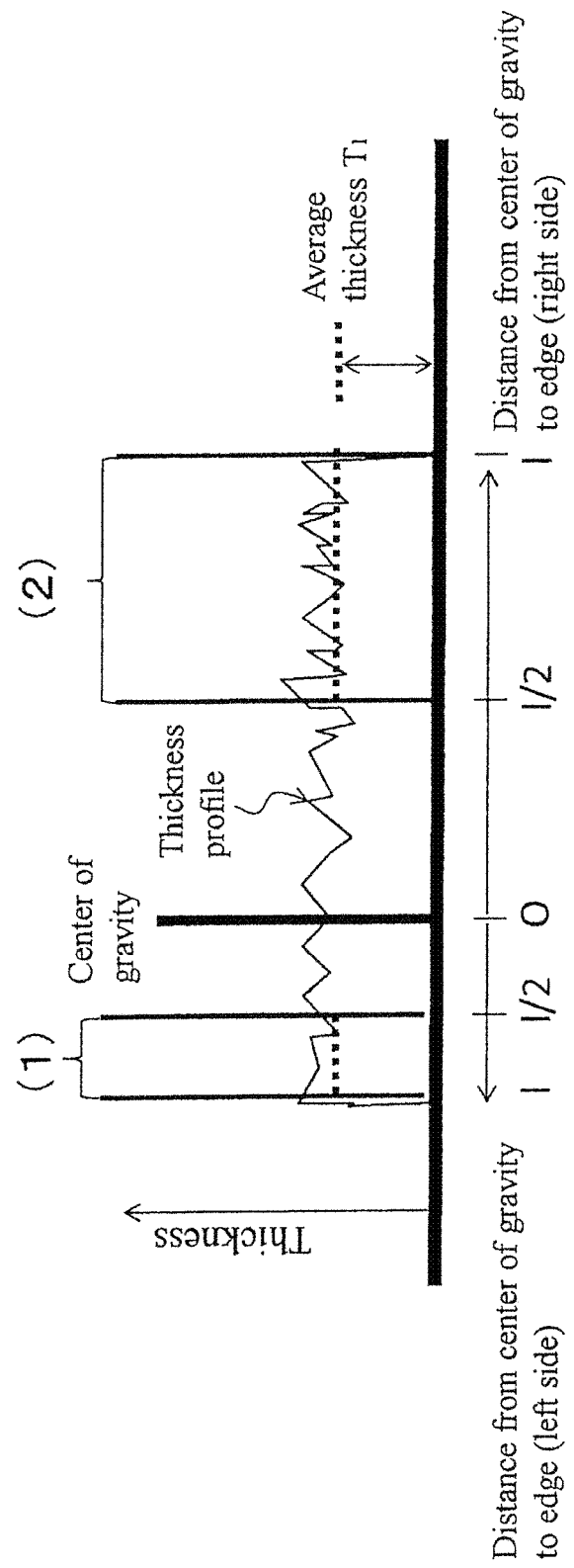

FIG. 18 is a schematic diagram showing a measurement range of $T_1$ by AFM.

Figure 19:
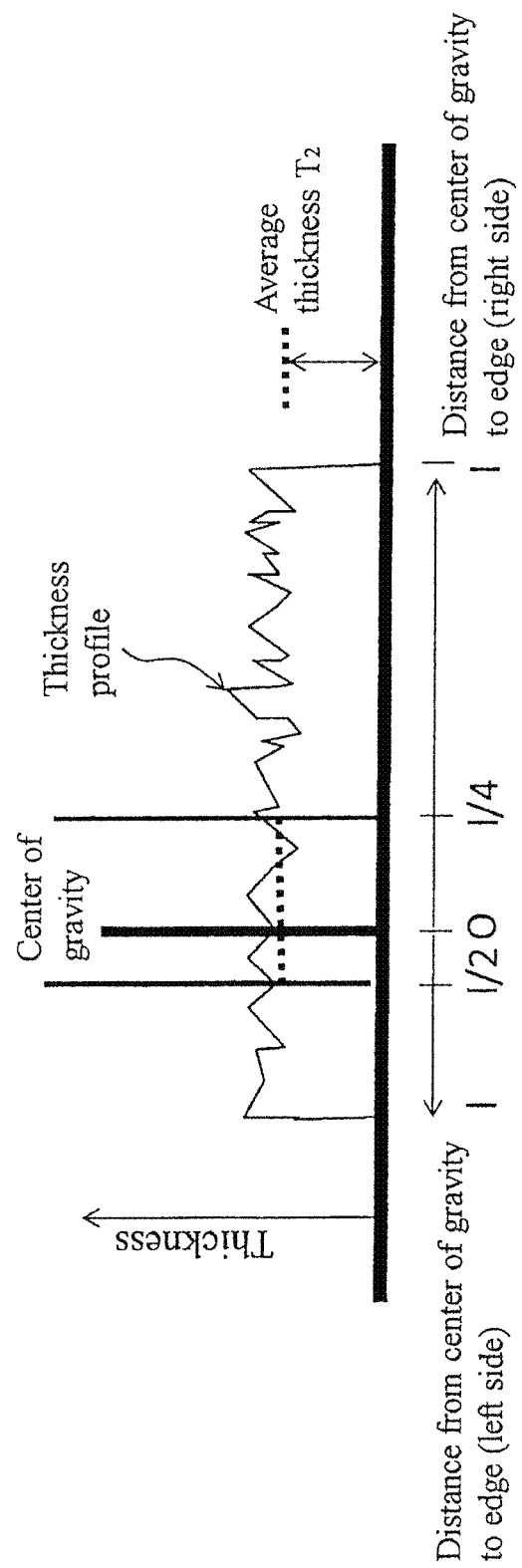

FIG. 19 is a schematic diagram showing a measurement range of $T_2$ by AFM.

Figure 20:
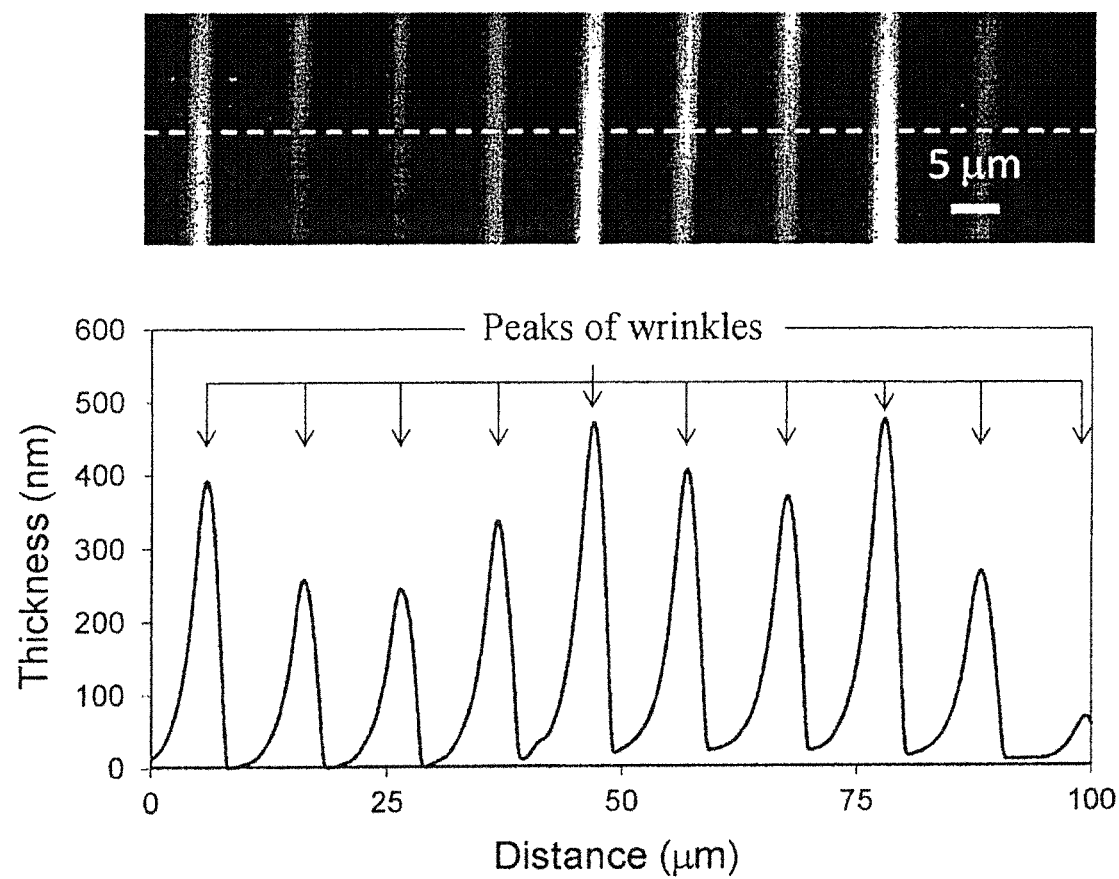

FIG. 20 is diagrams showing an example of an AFM image and a cross-sectional profile thereof by the SIEBIMM method.

EXPLANATION OF SYMBOLS

1: Dispersion liquid for a polymer film
2: Teflon (registered trademark) substrate
3: PVA aqueous solution
4: tweezers
5: polymer film agglomerate
6: purified water
7: $SiO_2$ substrate as a skin model
11: polymer film
12: PDMS piece
13: center line
14: wrinkle

DETAILED DESCRIPTION

Hereinafter, desirable examples will be explained in detail. The scope of this disclosure is not bound to these explanations, and even other than the exemplifications shown below can be appropriately changed and practiced as long as the desired effect(s) is not damaged.

Polymer Film

An average film thickness $T_0$ along a straight line D passing through a center of gravity of a two-dimensional projection such that the area of the polymer film is maximized, is 10 nm to 1000 nm from the viewpoint of shape followability to an adherend, preferably 10 nm to 500 nm, more preferably 20 nm to 300 nm, and particularly preferably 20 nm to 100 nm. If it is thinner than 10 nm, there is a possibility that it becomes difficult to maintain the shape of the polymer film itself, and if it exceeds 1000 nm, there is a possibility that the followability to the adherend is lost.

Here, $T_0$ means the average film thickness in the straight line D passing through the center of gravity of the two-dimensional projection such that the area of the polymer film is maximized.

Here, the "straight line D passing through the center of gravity of the two-dimensional projection" means the following $D_1$ to $D_4$:

(1) a minor axis passing through the center of gravity: $D_1$ (namely, it means a straight line passing through the center of gravity and becoming shortest with respect to the length of the line segment on the two-dimensional projection)

(2) a major axis passing through the center of gravity: $D_2$ (namely, it means a straight line passing through the center of gravity and becoming longest with respect to the length of the line segment on the two-dimensional projection)

(3) straight lines passing through the center of gravity and bisecting a wide angle and a narrow angle formed by the minor axis and the major axis respectively. $D_3$, $D_4$.

When the minor axis and the major axis are the same or there are a plurality of them, two lines having the smallest difference between the wide angle and the narrow angle formed by the minor axis and the major axis are selected.

Further, with respect to $T_0$, first, a thickness profile in the cross section of the straight line $D_1$ passing through the center of gravity is obtained and, then, as shown in FIG. 18, in the thickness profile of the cross section, an average value of the thicknesses from one side edge to the other side edge is calculated, similarly for each of $D_2$ to $D_4$, an average value of the thicknesses from one side edge to the other side edge is calculated, and an average value further calculated from the average values of the thicknesses calculated for $D_1$ to $D_4$ is referred to as an average film thickness $T_0$. Here, the thickness profile in the cross section and the average value of the thicknesses from one side edge to the other side edge are calculated using the AFM explained in the item of Examples.

Although the shape of the polymer film is not particularly limited, in the figure projected onto a two-dimensional plane such that the area of the polymer film is maximized, since it is not necessary to be geometrically complete and it may be recognized to be resembled to each shape, for example, circular, elliptical, approximately circular, approximately elliptical, approximately polygonal, ribbon shape, or the like can be exemplified, and it is preferred that the shape of the polymer film is at least one shape selected from the group consisting of a circle, an ellipse, an approximately circular shape, an approximately elliptical shape, an approximately polygonal shape and a ribbon-like shape. An approximately circular shape and an approximately elliptical shape are more preferable from the viewpoint of easiness of overlapping of polymer films.

The size of the polymer film can be represented by the following method. Namely, in the above-described figure projected on the two-dimensional plane such that the area of the polymer film is maximized, the average value L of the distances 1 from the center of gravity to the edges is 0.1 µm≤L≤500 µm, preferably 0.1 µm≤L≤250 µm, and more preferably 0.1 µm≤L≤50 µm. If the average value L of the distances 1 from the center of gravity to the edges becomes smaller than 0.1 µm, there is a possibility that the polymer film agglomerate is poor in stability because the polymer films are difficult to overlap each other, and if it becomes larger than 500 µm, there is a possibility that the dispersibility to water or the like becomes poor. Here, the average value L of the distances 1 from the center of gravity to the edge is determined by obtaining the thickness profile in the cross section of the straight line $D_1$ passing through the center of gravity, and then as shown in FIG. 18, in the thickness profile in the cross section, determining the distance 1 (left side) from the center of gravity to the edge and the distance 1 (right side) from the center of gravity to the edge, respectively, and determining a value averaged with them (this is referred to as the average value $L_1$). Similarly for $D_2$ to $D_4$, $L_2$ to $L_4$ are determined, and a value averaged with $L_1$ to $L_4$ is referred to as the average value L of the distances 1 from the center of gravity to the edges. Here, the thickness profile in the cross section and the average value L of the distances 1 are calculated using the AFM explained in the item of Examples.

In the polymer film, the thickness deviation $\Delta = 1 - T_1/T_2$ is $0.346E \times 10^{-9} - 1.499 < \Delta < -0.073E \times 10^{-9} + 0.316$, and preferably $0.346E \times 10^{-9} 1.352 < \Delta < -0.068E \times 10^{-9} + 0.264$.

When the Young's modulus E and the deviation A do not satisfy the above-described relationship, the polymer film agglomerate is poor in "self-supportability." The "self-supportability" mentioned herein means a property that a polymer film agglomerate does not require a supporting material to maintain the structure as a single film in its accumulated state. However, this does not exclude that the polymer film and its agglomerate form a supporting material and a composite material.

Here, $T_1$ and $T_2$ represent, in the straight lines D passing through the center of gravity of the two-dimensional projection such that the area of the polymer film is maximized, $T_1$: an average film thickness of a region from ½ to 1 of the distance 1 from the center of gravity to the edge, and $T_2$: an average film thickness of a region from the center of gravity to ¼, and E represents Young's modulus.

Here, the "straight lines D passing through the center of gravity of two-dimensional projection" means the followings as described above:
(1) a minor axis passing through the center of gravity: $D_1$,
(2) a major axis passing through the center of gravity: $D_2$,
(3) straight lines passing through the center of gravity and bisecting a wide angle and a narrow angle formed by the minor axis and the major axis respectively: $D_3$, $D_4$.

When the minor axis and the major axis are the same or there are a plurality of them, two lines having the smallest difference between the wide angle and the narrow angle formed by the minor axis and the major axis are selected.

Here, each "average film thickness" means an average value calculated using the four straight lines $D_1$ to $D_4$ selected according to the above. Concretely, first, a thickness profile in the cross section of the straight line $D_1$ passing through the center of gravity is obtained.

Next, as shown in FIG. 18, in the thickness profile of the cross section, with respect to the distance 1 (left side) from the center of gravity to the edge, the average thickness (1) of the thickness in ½ to 1, and with respect to the distance 1 (right side) from the center of gravity to the edge, the average thickness (2) in ½ to 1, are determined respectively, and a value further averaged with those average thicknesses (1) and (2) is determined. This is similarly determined also for $D_2$ to $D_4$, and a value averaged with them is referred to as $T_1$.

Similarly, with respect to $T_2$, a thickness profile in the cross section of the straight line $D_2$ passing through the center of gravity is obtained, as shown in FIG. 19, in the thickness profile of the cross section, with respect to the distance 1 (left side) from the center of gravity to the edge, the average thickness of the thickness in the center of gravity to ¼, and with respect to the distance 1 (right side) from the center of gravity to the edge, the average thickness in the center of gravity to ¼, are determined respectively, and a value further averaged with those average thicknesses is determined. This is similarly determined also for $D_2$ to $D_4$, and a value averaged with them is referred to as $T_2$. Here, the thickness profile in the cross section, $T_1$ and $T_2$ are calculated using AFM (Atomic Force Microscope) explained in the item of Examples.

Young's modulus E of the polymer film is 0.01 GPa≤E≤4.3 GPa, and preferably 0.01 GPa≤E≤3.9 GPa. If Young's modulus E is less than 0.01 GPa, the polymer film easily deforms during handling of the polymer film and the polymer films tend to aggregate easily, resulting a poor dispersibility in a liquid medium, and if greater than 4.3 GPa, there is a possibility that the flexibility of the polymer film becomes poor and the followability to the adherend becomes poor.

For the calculation of Young's modulus E of the polymer film, Strain-Induced Elastic Buckling Instability for Mechanical Measurements (SIEBIMM) method is used (C. M. Stafford et al., Nature Materials 2004, 3, 545-550). This is a method of measuring Young's modulus from the wavelength of the buckling phenomenon occurring in the polymer film in a direction perpendicular to a compression or stretching direction when compressing or stretching the polymer film stuck on polydimethylsiloxane (PDMS). Since the film thickness of the polymer film includes that in case where there is a variations in film thickness, one calculated by the method explained in the item of Examples is referred to as Young's modulus E. First, the relationship between Young's modulus and average film thickness h (h is the same value as that of the aforementioned $T_0$) of a smooth polymer film (5 mm square) prepared by spin coating method is calculated by SIEBIMM method for each kind of polymer. The Young's modulus E of each polymer film is calculated from the average film thickness h (h is the same value as that of the aforementioned $T_0$) by using the above-described relationship between the film thickness and Young's modulus.

Kind of Polymer

The polymer forming the polymer film is not particularly limited, and a polymer having a performance according to its use can be selected, preferably a polymer having a compatibility to an organism.

It is a sole polymer and/or a polymer containing a copolymer containing at least one kind of polymer selected form:
(1) a polyester-based resin such as polylactic acid, polyglycolic acid, polydioxanone or polycaprolactone,
(2) a polyether-based resin such as polyethylene glycol,
(3) a polymethacrylate-based resin such as polymethyl methacrylate, polyethyl methacrylate or polyhydroxyethyl methacrylate,
(4) a polysaccharide or a polysaccharide ester such as cellulose acetate, alginic acid or chitosan, (5) a polyvinyl-based resin such as polyvinyl acetate, polyvinyl alcohol or polyvinyl pyrrolidone, and from the viewpoint of economy, polylactic acid, polyglycolic acid, polydioxanone, polycaprolactone, polyethylene glycol, polymethyl methacrylate and as copolymer thereof are in ore preferred.

Production Method of Polymer Film

Next, a typical production method of the polymer film will be described.

Although the method of producing the polymer film is not particularly limited, exemplified are a micro contact printing method using a silicone rubber or the like, a phase separation method (a method forming a film in which phase separation is caused by two kinds of polymers not mixed with each other, and selectively dissolving and removing one polymer by immersing the film in a solvent corresponding to a good solvent for one polymer and a poor solvent for the other polymer), a method of adhering a droplet to a base material and thereafter drying, an ink jet printing method, a method of obtaining a pattern-like polymer film by photolithography and the like.

The polymer film can be obtained as a dispersion liquid by peeling the prepared polymer film from a base material, for example, by laminating it together with the base material and a water-soluble film in any of the following orders:

(1) base material/water-soluble film/polymer film
(2) base material/polymer film/water-soluble film.

In lamination in the order described in (1), a polymer film dispersion liquid is obtained by immersing it in an aqueous solution together with the base material to dissolve the water-soluble film, thereafter removing the base material and removing the aqueous solution in which the water-soluble film is dissolved. In lamination in the order described in (2), dispersion liquid for a polymer film is obtained by peeling the water-soluble film together with the polymer film from the base material using tweezers or the like, thereafter immersing it in an aqueous solution to dissolve the water-soluble film, and removing the aqueous solution in which the water-soluble film is dissolved.

Although the method of removing the aqueous solution in which the water-soluble film is dissolved is not particularly limited, a centrifugation method, an ultrafiltration method, or the like can be exemplified.

Although the kind of the base material is not particularly restricted, a silicon substrate, a glass substrate, a polyethylene film, a polypropylene film, a polyethylene terephthalate film, a polycarbonate film, a polyimide film, an acrylic film, a polyamide film, a fluorine film and the like can be exemplified, and preferably, it is a silicon substrate, a polypropylene film or a polyethylene terephthalate film from the viewpoint of economy, more preferably a silicon substrate or a polyethylene terephthalate film.

Although the thickness of the base material is not particularly limited, it can be 5 µm to 1000 µm, and from the viewpoint of economy, preferably 5 µm to 500 µm, more preferably 10 µm to 300 µm.

Although the polymer to be used for the water-soluble film is not particularly limited, polyvinyl alcohol, alginic acid, pullulan, polyvinyl pyrrolidone, collagen, starch, agar, chitosan, dextran, polyacrylic acid, polyethylene glycol and the like can be exemplified, and from the viewpoint of economy, preferably it is polyvinyl alcohol or pullulan, more preferably polyvinyl alcohol.

Although the method of applying the water-soluble film is not particularly limited, a solution is applied to the base material, for example, by a method such as spin coating, spray coating, bar coating, dip coating, casting, gravure printing, screen printing, or ink jet printing. Although the thickness of the water-soluble film is not particularly limited, it may be 5 nm to 100 µm.

When micro contact printing method is used as the method of producing the polymer film, first, a master substrate having a desired pattern is prepared. The master substrate is obtained, for example, by forming a photoresist on a silicon substrate by a manner such as spin coating, irradiating ultraviolet rays through a photomask having a desired pattern, and then etching with a solvent.

By stamping the above-described master substrate with an elastomer or the like, a stamper (printing original plate) is obtained. For example, a PDMS stamper (relief printing original plate) having a reversed pattern of the master substrate is obtained by pouring a prepolymer solution of PDMS into the master substrate, curing it by heating, and then peeling the cured PDMS from the master substrate.

To the above-described stamper, a coating material dissolved with a desired polymer is applied. Although the method of applying the coating material to the stamper is not particularly limited, for example, a spin coating method, a spray coating method, a bar coating method, a dip coating method and the like can be exemplified. The mass concentration of the polymer of the coating material is usually 0.1 mass % to 20 mass %, preferably 0.3 mass % to 10 mass %.

In using the spin coating method, for example, the solution may be applied on the stamper by a spin coater, preferably at 500 rpm to 7000 rpm for 10 seconds to 30 seconds, more preferably at 100 rpm to 3000 rpm for 15 seconds to 25 seconds.

The polymer film can be transferred by bringing the stamper coated with the polymer solution into contact with another base material.

As the method of producing the polymer film, in utilizing phase separation by two kinds of polymers which are not mixed with each other, first, the above-described two kinds of polymers are dissolved at an arbitrary ratio in a first solvent to prepare a solution. The first solvent is not particularly limited as long as it can dissolve two or more kinds of polymers. The total mass concentration of the polymer in the solution is usually 0.1 mass % to 20 mass %, preferably 0.3 mass % to 10 mass %. Next, after applying the prepared solution to the base material, the first solvent is removed from the solution applied to the base material, whereby a polymer film phase-separated into a sea-island structure can be obtained. Next, by immersing the polymer film phase-separated into a sea-island structure in a second solvent which is a poor solvent for the polymer of the island part as well as a good solvent for the polymer of the sea part, and removing the sea part, a polymer film can be obtained. In this method, it is possible to control the size and shape of the polymer film to be produced by adjusting the mass ratio or the solid concentration of each polymer when preparing the solution dissolved with two kinds of polymers.

Although the method of applying the solution to the base material is not particularly limited, the solution is applied thinly to the base material by a method such as a spin coating method, a spray coating method, a bar coating method, a dip coating method, gravure printing, screen printing, ink jet printing. Preferably, a method of laminating by a roll-to-roll method by a gravure method is employed.

More concretely, for example, when polystyrene and poly-DL-lactic acid, ethyl acetate are used as the first solvent and cyclohexane is used as the second solvent, or when polyvinylpyrrolidone and polystyrene, dichloromethane are used as the first solvent and water is used as the second solvent, or when polyvinyl acetate-polyvinylpyrrolidone copolymer and poly DL lactic acid, acetone are used as the first solvent and water is used as the second solvent, or when polyvinyl pyrrolidone and poly-L-lactic acid-polyethylene glycol copolymer, dichloromethane are used as the first solvent and water is used as the second solvent or the like, can be exemplified.

Polymer Film Agglomerate

The polymer film agglomerate is a "film-like structure" in which the polymer films are integrated and spread in a sheet-like shape at a state where at least a part of the polymer films are in close contact with each other. The polymer film agglomerate can be obtained by dropping or blowing a dispersion liquid, in which the polymer films are dispersed in a liquid medium, to the surface of the adherend and then removing the liquid solvent by drying. Alternatively, another method of treating a plurality of the polymer films gathered at a dry state as a flake-like "aggregate," spraying the flake aggregate onto the surface of the adherend, thereafter, spraying the liquid solvent further onto the surface appropriately, and drying and removing the liquid solvent, may be employed. In the above-described film-like structure, there may be holes composed of gaps between polymer films. Further, the "aggregate" referred to here means a state in which the polymer films do not form a film-like structure adhered to each other, but is easily dispersed by an external force.

Although the drying method to obtain the above-described "aggregate" is not limited, for example, freeze drying, vacuum drying, air stream drying, rotary drying, stirring drying, spray drying, or the like can be exemplified, and in particular, the spray drying is more preferred.

EXAMPLES

Hereinafter, our films, liquids and agglomerates will be further explained with reference to examples.
Polymer Used
Water-Insoluble Polymer-1
Polystyrene (PS): supplied by Corporation, weight average molecular weight Mw: 280,000.
Water-Insoluble Polymer-2
Polymethyl methacrylic acid (PMMA): supplied by Sigma-Aldrich Corporation, weight average molecular weight Mw: 120,000.
Water-Insoluble Polymer-3
Poly-DL-lactic acid (PDLLA): supplied by PURAC Corporation, PURASORB (registered trademark) PDL 20, weight average molecular weight Mw converted to PS: 140,000.
Water-Insoluble Polymer-4
PLLA-4 PEG: In a nitrogen stream, 75 g of L-lactide (supplied by PURAC Corporation) and 25 g of dehydrated 4-branched polyethylene glycol (4PEG) derivative "Sunbright PTE-10000" supplied by NOF Corporation) having an average molecular weight of 10,000 were mixed and dissolved and mixed at 140° C., and then, 8.1 mg of tin dioctanoate (supplied by Wako Pure Chemical Industries, Ltd.) was added at 180° C. to cause reaction, thereby obtaining a block copolymer of polylactide-4-polyethylene glycol. This block copolymer was dissolved in chloroform, washed with dilute hydrochloric acid, and then, a precipitate prepared by dropping it into a large excess of methanol was obtained as a water-insoluble polymer (PLLA-4PEG) (PLLA: poly-L-lactic acid). The weight average molecular weight according to GPC (Gel Permeation Chromatography) method (PMMA standard) was 85,000, and the unit ratio of lactic acid/ethylene glycol calculated by NMR (Nuclear Magnetic Resonance) method was 3/1.

Water-Soluble Polymer-1
Polyvinyl alcohol (PVA): supplied by Kanto Chemical Co., Ltd., weight average molecular weight Mw: 22,000.
Water-Soluble Polymer-2.
Polyvinylpyrrolidone (PVP): supplied by Wako Pure Chemical Industries, Ltd., weight average molecular weight Mw: 40.000.
Water-soluble Polymer-3
Polyvinylpyrrolidone-polyvinyl acetate copolymer (PVP-PVAc): supplied by BASE Corporation, weight average molecular weight Mw: 40,000.
Base Material Used
Polyethylene terephthalate film (PET film): "Lumirror (registered trademark)" type T60, supplied by foray Industries, Inc., thickness 25 µm
Silicon substrate: supplied by KST World Corporation, P type silicon wafer, oxide film 200 nm, crystal plan (100), diameter 100±0.5 mm, thickness 525±25 µm
Film Forming Method by Gravure Method A film was formed on a PET film having a width of 12 cm by using a micro gravure printing apparatus (supplied by Yasui Seiki Co., Ltd., mini-laboratory apparatus). A water-soluble film with a thickness of 100 nm was formed on one surface of the PET film using a 2 mass % PVA aqueous solution and, then, using a solution prepared by dissolving each of various kinds of polymers shown in Examples and Comparative Examples on the PVA film, a polymer film having a desired thickness was formed. As the conditions of the mini-laboratory apparatus at this time, the rotational speed of the gravure roll was 30 rpm, the line speed was 1.3 m/min, and the drying temperature was 100° C. in case of aqueous solution, and 80° C. in case of organic solutions (dichloromethane solution, acetone solution, ethyl acetate solution).
Film Forming Method by Micro Contact Printing Micro contact printing was carried out by a soft lithography technology as follows. A negative photoresist (supplied by Nippon Kayaku Co., Ltd., SU-8, 3005) was formed as a film on a silicon substrate using a spin coater (supplied by Mikasa Co., Ltd., Opticoat MS-A150) (500 rpm, 10 seconds, slope 10 seconds, 4000 rpm, 30 seconds, slope 5 seconds). Thereafter, after heating (100° C., 5 minutes) with a hot plate, exposure was carried out using a photomask in which circular chromium patterns each having a diameter of 100 µm were arranged at intervals of 50 µm and 100×100 on 1.5×1.5 cm$^2$ sides, and after further heating with the hot plate (for 3 minutes at 75° C. and for 3 minutes at 100° C.), washing was carried out with 1-methoxy-2-propyl acetate (SU-8 developer), isopropyl alcohol and water, and further heating was carried out with the hot plate (150° C., 10 minutes). Hereinto, a prepolymer solution of PDMS (supplied by Dow Corning Toray Co., Ltd., SYLGARD (registered trademark) 184 silicone elastomer kit) was poured, and by solidifying it, a PDMS stamper having a circular pattern with a diameter of 100 µm was prepared. On this PDMS stamper, solutions dissolved with the respective polymers shown in Examples and Comparative Examples were coated by spin coating, respectively. A PDMS stamper coated with a solution was brought into contact with a silicon substrate or a PET film on which 2 mass % PVA had been formed as a film for several seconds to transfer a film of a circular portion on the PDMS stamper, and by drying it, a polymer film with a disk-like form was obtained.
Film Forming Method by Spin Coating Method Opticoat MS-A150, supplied by Mikasa Co., Ltd., was used as a spin coater. A water-soluble sacrificial film was formed on a silicon substrate using a 2 mass % PVA aqueous solution (4000 rpm, 40 seconds), and then a polymer film with a desired thickness was formed using a solution in which a polymer shown in Comparative Example was dissolved (4000 rpm, 20 seconds).

Evaluation of Shape and Film Thickness of Prepared Polymer Film

Dispersion liquid for the prepared polymer was dropped onto a silicon substrate, polymer films were adsorbed to not overlap with each other, and after dried in a vacuum dryer for 24 hours, the shape was evaluated at a room temperature (25° C.±2° C.) using an AFM (supplied by KEYENCE CORPORATION, atomic force microscope VN-8000).

In the figure projected on a two-dimensional plane such that the area of the prepared polymer film is maximized, using the four straight lines $D_1$ to $D_4$ passing through the center of gravity, the average film thicknesses $T_0$, $T_1$ and $T_2$ and the average value L of the distance 1 from the center of gravity to the edge were measured. Where, in the AFM measurement, with respect to the film thickness T of the polymer film, $T_0$, $T_1$, and $T_2$ were calculated as the heights from the silicon substrate where the polymer film was not present. Further, when it was difficult to distinguish the edge of the polymer film, in the profile of the thickness in the cross section, a point where the film thickness became 5 nm for the first time in the profile of the thickness from the center of gravity of the polymer film toward the edge was regarded as an edge. For analysis of the thickness, software supplied by KEYENCE CORPORATION (VN Analyzer) was used.

Determination of Polymer Film Content of Prepared Dispersion Liquid for Polymer Film The polymer film content of dispersion liquid for each polymer film, prepared was determined by the following method.

Water-Insoluble Polymer-1

After drying the solvent, dispersion liquid for the PS film was dissolved in dichloromethane and the absorbance at the absorption wavelength λ=261 nm was measured with an ultraviolet-visible light absorption photometer (supplied by Nippon Bunko Corporation, V-660). PS dichloromethane solutions with different concentrations were prepared using raw material PS and the PS film content in dispersion liquid for the PS film was quantified using a calibration curve prepared from each absorbance.

Water-Insoluble Polymers-2 to 4

The concentration of the polymer film made of the other polymer was determined by dropping and drying a sufficiently diluted polymer film dispersion liquid on a sensor chip with a crystal oscillator microbalance (supplied by Initium Corporation, AFFINIX QN), and then quantified.

Determination Method of Young's Modulus of Polymer Film

As shown in FIG. 17, a polymer film 11 (5 mm square) prepared by a spin coating method was scooped onto a PDMS piece 12 (3.0 cm×3.0 cm, thickness: about 2 mm) which was stretched by about 3%, and then dried by vacuum drying for 12 hours. The wrinkle interval (λ) on the center line of the wrinkle occurring in the polymer film 11 perpendicular to the stretched direction when the PDMS piece 12 stretched in a uniaxial direction was restored was measured by AFM (room temperature: 25±2° C.). The center line 13 means one straight line passing through the center of gravity of one polymer film 11 and parallel to the stretching direction when the polymer film 11 is viewed from the upper side. At this time, the interval (λ) of the wrinkles 14 was measured for each of the left and right five polymer films from one polymer film using as a reference for determining the center line.

The interval of wrinkles means a distance from the origin of one wrinkle to the apex of another adjacent wrinkle on the center line. The "λ" was calculated as an average value of the intervals between the apexes of the wrinkles corresponding to a total of 10 wrinkles as sum of each 5 wrinkles on each one side of the center line extending from the center of gravity toward the two edges. When wrinkles did not occur at a condition of over 5 intervals on one side, it was defined as an average value of the intervals between the apexes of all wrinkles formed from one edge on the center line to the other edge. Young's modulus ($E_F$) of the polymer film was calculated using Equation (1) when the film thickness was referred to as an average film thickness h (equivalent to $T_0$), Young's modulus of the PDMS piece was referred to as $E_{PDMS}$, Poisson's ratio of the PDMS piece was referred to as $v_{PDMS}$ and Poisson's ratio of the polymer film was referred to as $v_F$.

$$E_F = 3 \frac{E_{PDMS}(1-v_F^2)}{1-v_{PDMS}^2} \left(\frac{\lambda}{2\pi h}\right)^3 \quad (1)$$

Figure 2:
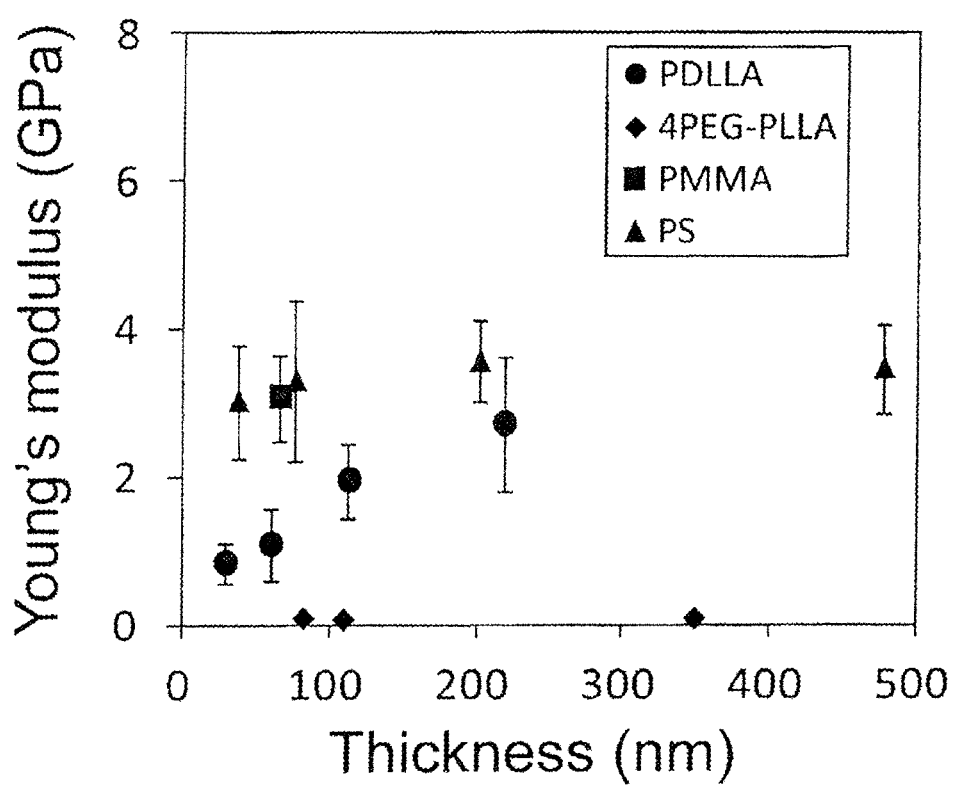
FIG. 2 is a graph showing the relationship between film thickness and Young's modulus of various polymer films calculated by the SIEBIMM method.

Poisson's ratio and Young's modulus of PDMS, and Poisson's ratio of polymer film were measured according to JIS K7161: 2014. The Poisson's ratio of the PDMS piece used in Examples and Comparative Examples was 0.5 and the Young's modulus of PDMS was 1.8 MPa. Further, Young's modulus of each polymer film shown in Examples and Comparative Examples was determined from the relationship between Young's modulus and the film thickness calculated here (FIG. 2). Accompanying with increase of the film thickness, there is a possibility that wrinkles on the polymer film may not be observed by the difference in color density due to microscopic observation. In that case, the tensile elastic modulus of the polymer used for preparing the polymer film is calculated according to the method described in JIS K7161: 2014, and the calculated value is used as the Young's modulus of the corresponding polymer film.

Calculation of Deviation of Polymer Film

The deviation Δ is defined by equation (d):

$$\Delta = 1 - T_1/T_2 \quad (d)$$

In FIG. 20, an AFM image (upper diagram in FIG. 20) and its cross-sectional profile (lower diagram in FIG. 20) according to the SIEBIMM method in case where the sample is polystyrene having a thickness of 202 μm are exemplified.

Sample: Polystyrene with a Thickness of 202 μm

Evaluation of Self-Supportability of Polymer Film Agglomerate

Figure 1:
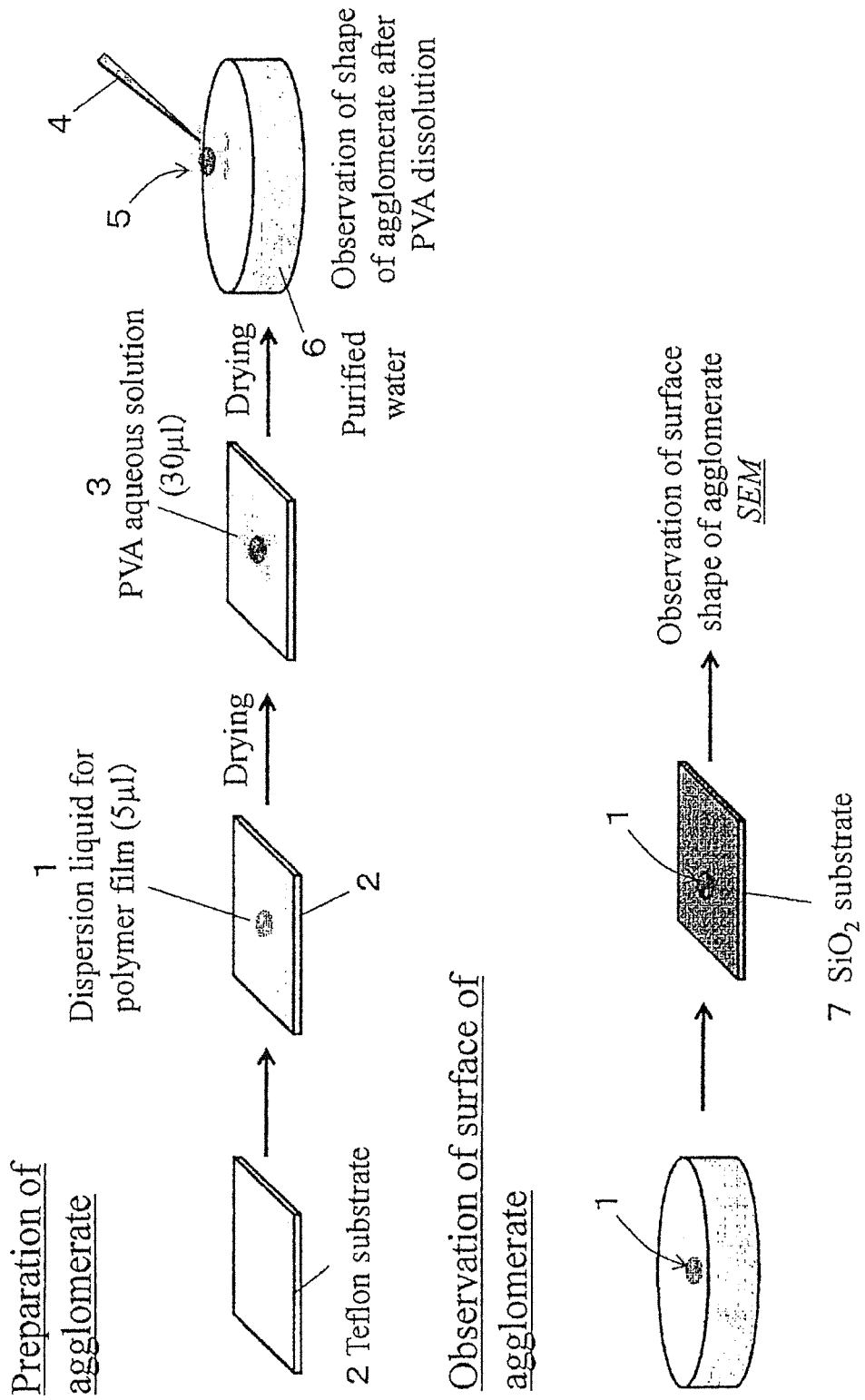
FIG. 1 is a schematic diagram showing examples of a method of preparing and a manner of observing a polymer film agglomerate.

Preparation of polymer film agglomerate and evaluation of self-supportability at gas-liquid interface were carried out by the method described in FIG. 1. The concentration of the dispersion liquid 1 of the prepared polymer film was controlled at 1 mg/ml, and after it was dropped on the "Teflon (registered trademark)" substrate 2 and dried, 30 μl of 10 mass % PVA aqueous solution 3 was dropped thereonto. After drying at room temperature (25° C.±2° C.) for 24 hours or more, the polymer film "agglomerate" was peeled off from the "Teflon (registered trademark)" substrate 2 by peeling off the PVA film adhered with the polymer film by tweezers 4. The PVA film of the peeled PVA film-attached polymer film "agglomerate" 5 was spontaneously dissolved by floating on the water surface of the purified water 6 at a condition of the PVA side facing down, and the self-supportability (shape retaining property) was visually confirmed at the gas-liquid interface of the polymer film "agglomerate." A case where the agglomerate existed as one film after 15 minutes after floating on the surface of purified water was determined as rank A, and a case where it was disintegrated without being present as one film and dispersed in purified water was determined as rank B.

Coatability of Polymer Film Agglomerate on Skin Model

The concentration of the prepared dispersion liquid for the polymer film 1 was set at 1 mg/ml, and after it was dropped by 5 µl onto $SiO^2$ substrate 7 (supplied by Beaulax Co., Ltd., BIO SKIN NO. 47) as a skin model and dried, surface observation was performed by SEM (supplied by KEYENCE CORPORATION, scanning electron microscope VE-9800). A case where the polymer films overlapped each other and coated along the irregularities of the skin model was determined as rank A, and a case where they were not coated along the irregularities was determined as rank B.

Adherence of Polymer Film Agglomerate on Skin Model

The concentration of dispersion liquid for the prepared polymer film was controlled at 0.25 mg/ml, and the dispersion liquid was dropped by 5 µl onto the skin model 7 and dried (32±2° C., 50±5%). The adherence was evaluated with reference to the tape test described in JIS K5600-5-6: 1999. The test temperature was set at 32±2° C. and the humidity was set at 50±5%. The peeling test was carried out using a cellophane tape supplied by Nichiban Co. Ltd. (type CT-24, adhesive strength 4.0 N/cm) and a tape supplied by Sumitomo 3M Corporation (type 332, adhesive strength 0.22 N/cm) each with a width of 24 mm. The result was visually confirmed, and when the peeling ratio of the polymer film "agglomerate" was 65% or more, a rank "5" was determined 35% or more and less than 65% was determined as rank "4," 15% or more and less than 35% was determined as rank "3," 5% or more and less than 15% was determined as rank "2," less than 5% was determined as rank "1," and where peeling was not observed was determined as rank "0."

Example 1 (Phase Separation Method)

Figure 3:
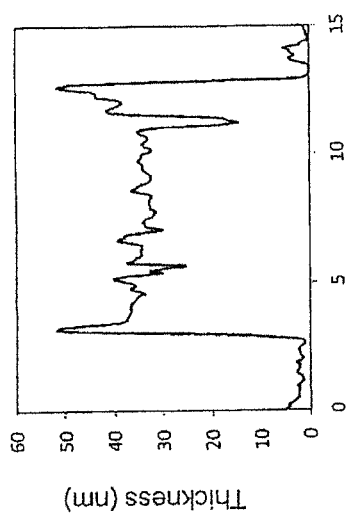
FIGS. 3A-3F show a PDLLA film prepared by a phase separation film of 2.0 mass % PDLLA:PS=1:4 (mass ratio) shown in Example 1. (A) shows an AFM image thereof, (B) is a cross-sectional view of a dotted line part in the AFM image, (C) is a diagram showing a self-supportability at a gas-liquid interface of an agglomerate of polymer film, (D) is an optical microscope image, (E) is a diagram showing an arm model, and (F) is an SEM image when the arm model is coated with a polymer film liquid dispersion.
Figure 3:
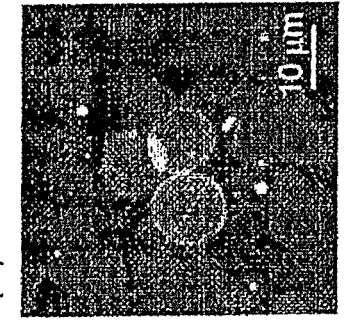
Figure 3:
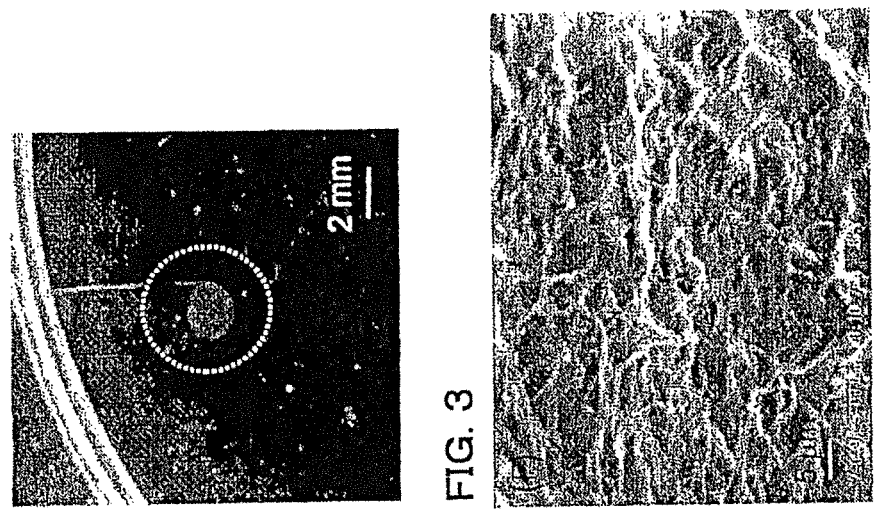
Figure 3:
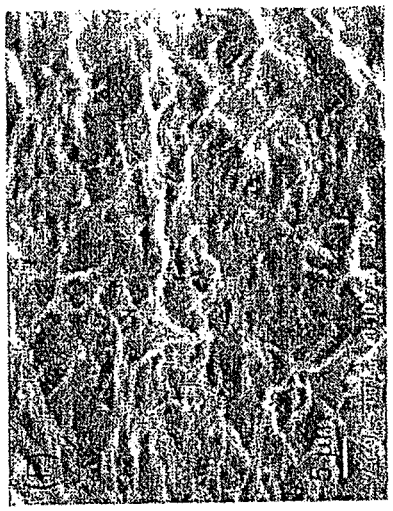
Figure 3:
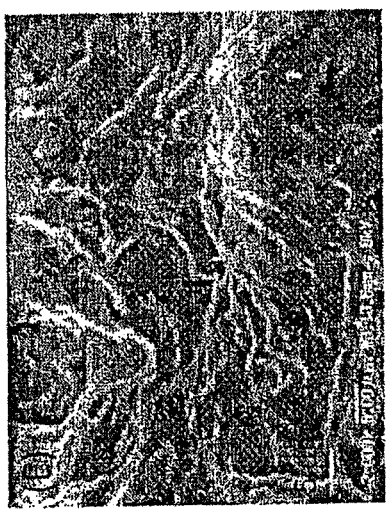
Figure 3:
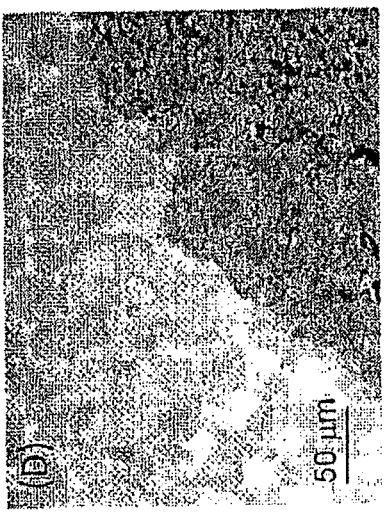

An ethyl acetate solution of 2.0 mass % PDLLA/PS=1/4 (mass ratio) was formed as a film by a gravure method on a PET film having formed with a 2.0 mass % PVA film thereon. The prepared PDLLA/PS film was formed as a PDLLA/PS phase separation film. Next, the PS region was removed by immersing the PDLLA/PS phase separation film in cyclohexane, and subsequently by immersing in purified water, the PVA film was dissolved. After the obtained solution was served to sonication treatment (20 kHz, 1 min) using a ultrasonic homogenizer (supplied by BRANSON CORPORATION, SONIFIER Model 250), PVA was removed by centrifugal separation (4,000 rpm, 30 min, 3 times), and dispersion liquid for a PDLLA film was obtained. The evaluation results are shown in FIG. 3 and Table 1. This polymer film agglomerate exhibited self-supportability at the gas-liquid interface (FIG. 3(C)), and polymer films were overlapped with each other and existed as a single film (FIG. 3(D)). It was observed that on the skin model, the agglomerates were coated following the irregularities of the skin model (FIG. 3(F)), and these agglomerates were not peeled off by the test with the tape having an adhesive strength of 0.22 N/cm, thereby exhibiting a high adherence.

Example 2 (Phase Separation Method)

Figure 4:
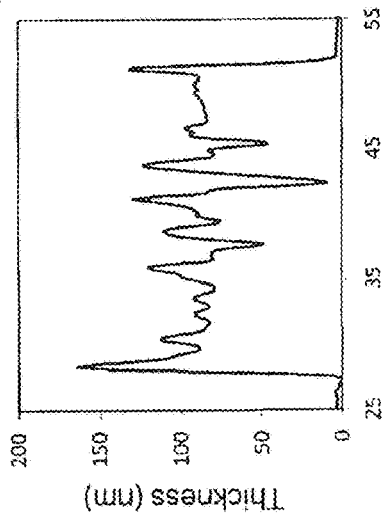
FIGS. 4A-4E show a PDLLA film prepared by a phase separation film of 2.5 mass % PDLLA:PS=1:4 (mass ratio) shown in Example 2. (A) shows an AFM image thereof, (B) is a cross-sectional view of a dotted line part in the AFM image, (C) is a diagram showing a self-supportability at a gas-liquid interface of an agglomerate of polymer film, (D) is an optical microscope image, and (E) is an SEM image when an arm model is coated with dispersion liquid for a polymer film.
Figure 4:
Figure 4:
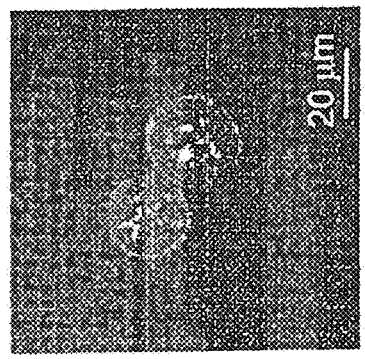
Figure 4:
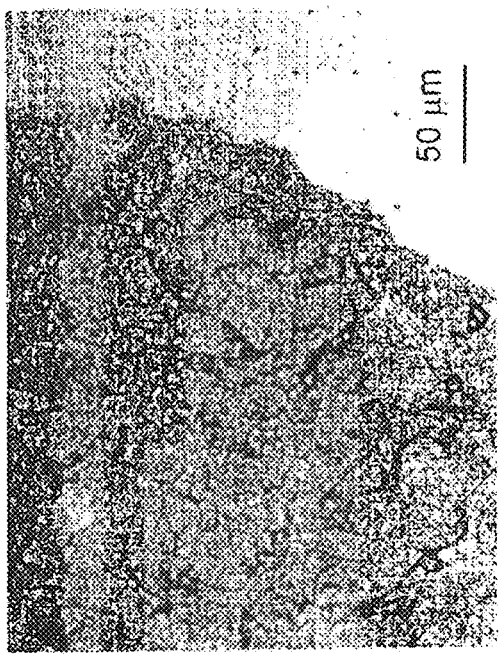

Dispersion liquid for a PDLLA film was prepared in the same manner as in Example 1 except that the concentration of the mixed solution of PDLLA and PS was set at 2.5 mass %. The evaluation results are shown in FIG. 4 and Table 1. This polymer film agglomerate exhibited self-supportability at the gas-liquid interface (FIG. 4(C)), and polymer films were overlapped with each other and existed as a single film (FIG. 4(D)). It was observed that on the skin model, the agglomerates were coated following the irregularities of the skin model (FIG. 4(E)), and these agglomerates were not peeled off by the test with the tape having an adhesive strength of 0.22 N/cm, thereby exhibiting a high adherence.

Example 3 (Phase Separation Method)

Figure 5:
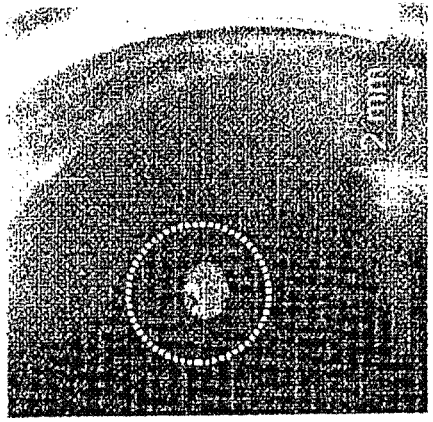
FIGS. 5A-5E show a PDLLA film prepared by a phase separation film of 3.0 mass % PDLLA:PS=1:4 (mass ratio) shown in Example 3. (A) shows an AFM image thereof, (B) is a cross-sectional view of a dotted line part in the AFM image, (C) is a diagram showing a self-supportability at a gas-liquid interface of an agglomerate of polymer film, (D) is an optical microscope image, and (E) is an SEM image when an arm model is coated with dispersion liquid for a polymer film.
Figure 5:
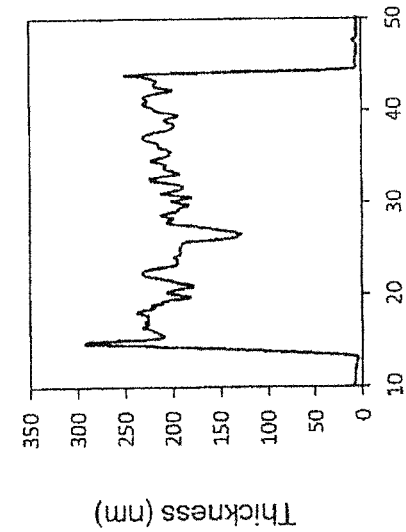
Figure 5:
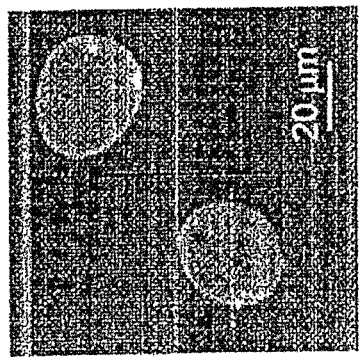
Figure 5:
Figure 5:
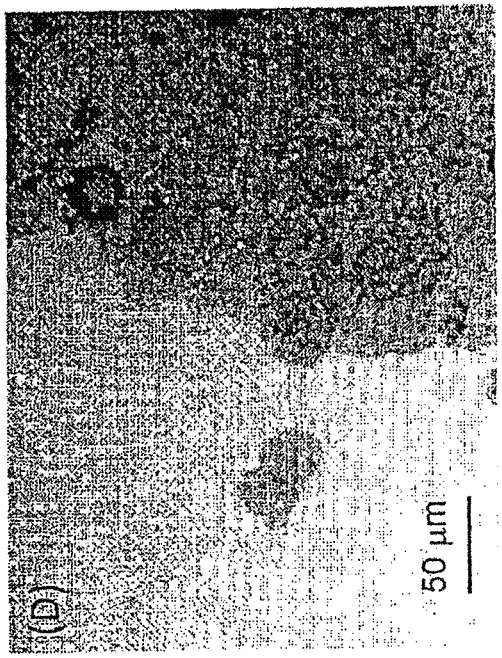

Dispersion liquid for a PDLLA film was prepared in the same manner as in Example 1 except that the concentration of the mixed solution of PDLLA and PS was set at 3.0 mass %. The evaluation results are shown in FIG. 5 and Table 1. This polymer film agglomerate exhibited self-supportability at the gas-liquid interface (FIG. 5(C)), and polymer films were overlapped with each other and existed as a single film (FIG. 5(D)). It was observed that on the skin model, the agglomerates were coated following the irregularities of the skin model (FIG. 5(E)), and these agglomerates were not peeled off by the test with the tape having an adhesive strength of 0.22 N/cm, thereby exhibiting a high adherence.

Example 4 (Micro Contact Printing Method)

Figure 6:
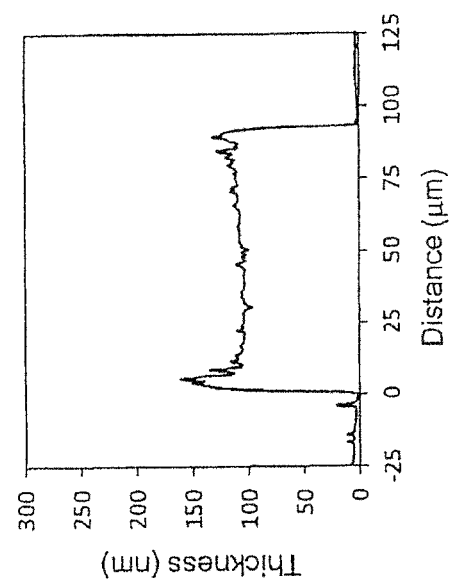
FIGS. 6A-6D show a PDLLA film prepared by micro contact printing using a 1.3 mass % PDLLA acetone solution shown in Example 4. (A) shows an AFM image thereof, (B) is a cross-sectional view of a dotted line part in the AFM image, (C) is a diagram showing a self-supportability at a gas-liquid interface of an agglomerate of polymer film, and (D) is an optical microscope image.
Figure 6:
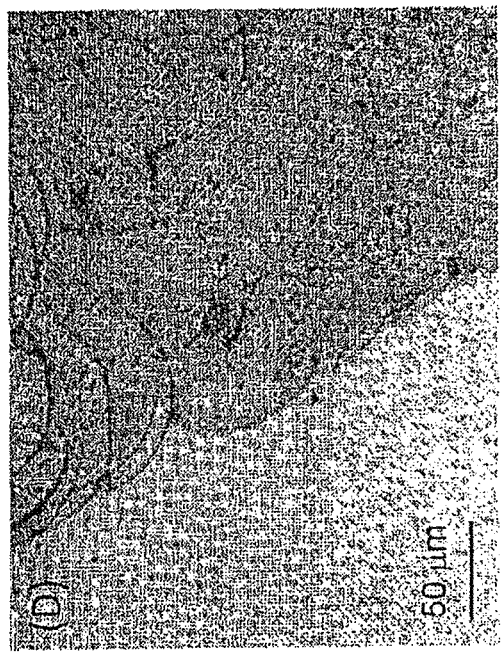
Figure 6:
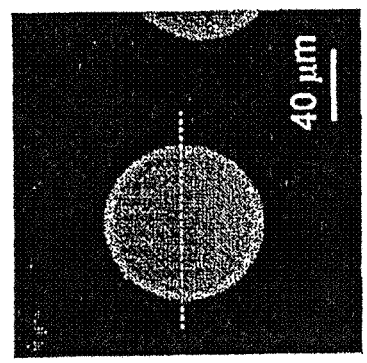
Figure 6:
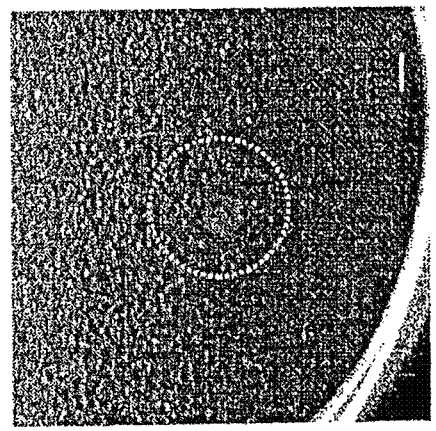

On a PDMS stamper, a 1.3 mass % PDLLA acetone solution was applied by spin coating (1,000 rpm, 25 seconds). The PDMS stamper applied with the solution was pressed onto a 2.0 mass % PVA film-formed PET film at a room temperature for several seconds to transfer the film of the circular part on the PDMS stamper, and by drying, a PDLLA film was obtained. The PDLLA film transferred onto the PET film was immersed in purified water, and PVA was dissolved the film was peeled off from the PET film. Centrifugal separation (4,000 rpm, 30 min, 3 times) was performed using a centrifugal separator, and PVA was removed to obtain dispersion liquid for a PDLLA film. The evaluation results are shown in FIG. 6 and Table 1. This polymer film agglomerate exhibited self-supportability at the gas-liquid interface (FIG. 6(C)), and the polymer films were overlapped with each other and existed as a single film (FIG. 6(D)).

Example 5 (Micro Contact Printing Method)

Dispersion liquid for a PLLA-4PEG film was obtained in the same manner as in Example 4 except that a 2.0 mass % PLLA-4PEG ethyl formate solution was applied on a PDMS stamper by spin coating (2,500 rpm, 20 seconds). The evaluation results are shown in FIG. 7 and Table 1. This polymer film agglomerate exhibited self-supportability at the gas-liquid interface (FIG. 7(C)), and the polymer films were overlapped with each other and existed as a single film (FIG. 7(D)). It was observed that on the skin model, the agglomerate was coated following the irregularities of the skin model (FIG. 7(E)).

Example 6 (Phase Separation Method)

Figure 8:
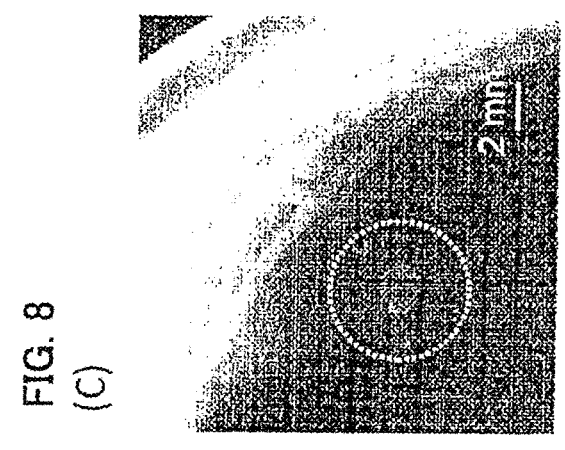
FIGS. 8A-8E show a PLLA-4 PEG film prepared by a phase separation film of a 2.0 mass % PLLA-4 PEG:PVP=1:4 (mass ratio) shown in Example 6. (A) shows an AFM image thereof, (B) is a cross-sectional view of a dotted line part in the AFM image, (C) is a diagram showing a self-supportability at a gas-liquid interface of an agglomerate of polymer film, (D) is an optical microscope image, and (E) is an AFM image different from that of (A).
Figure 8:
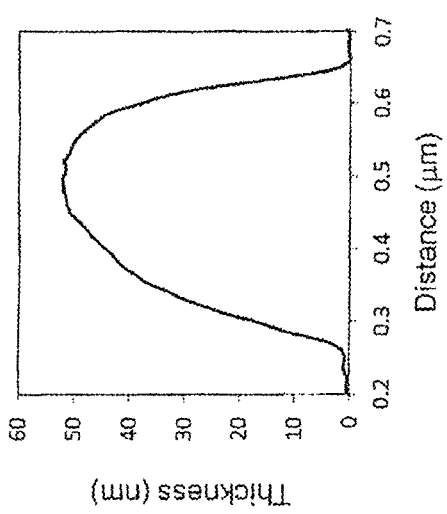
Figure 8:
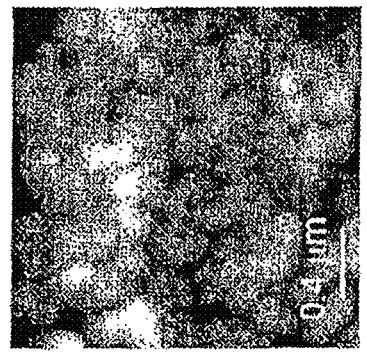
Figure 8:
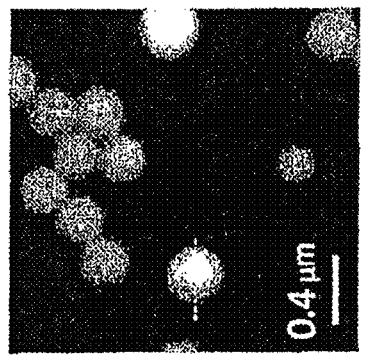
Figure 8:
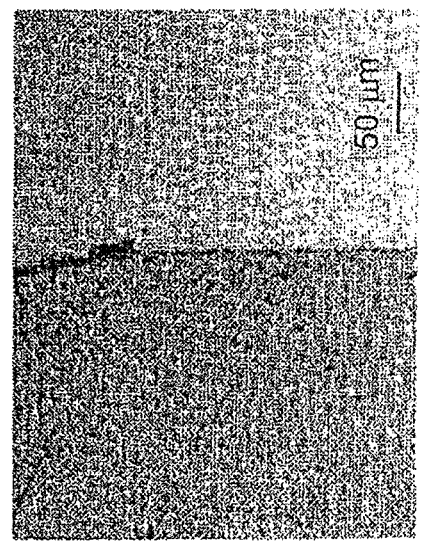

Dispersion liquid for aPLLA-4PEG film was prepared in the same manner as in Example 1 except that a dichloromethane solution having 2.0 mass % PLLA-4PEG/PVP=1/4 (mass ratio) was used. The evaluation results are shown in FIG. 8 and Table 1. This polymer film agglomerate exhibited self-supportability at the gas-liquid interface (FIG. 8(C)), and the polymer films were overlapped with each other and existed as a single film (FIGS. 8(D) and 8(E)).

Example 7 (Micro Contact Printing Method)

Figure 9:
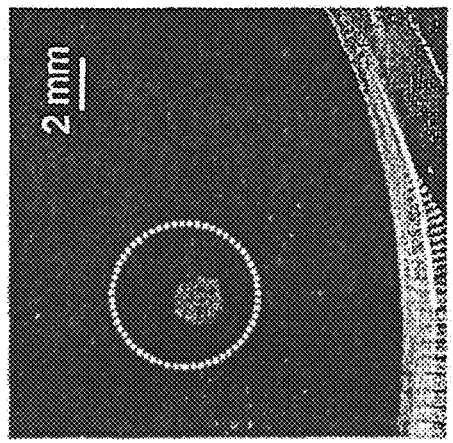
FIGS. 9A-9E show a PMMA film prepared by micro contact printing using a 1.5 mass % PMMA acetone solution shown in Example 7. (A) shows an AFM image thereof, (B) is a cross-sectional view of a dotted line part in the AFM image, (C) is a diagram showing a self-supportability at a gas-liquid interface of an agglomerate of polymer film, (D)
Figure 9:
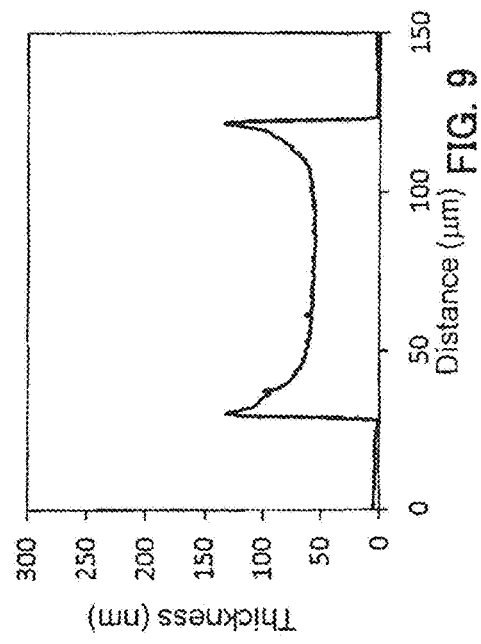
Figure 9:
Figure 9:
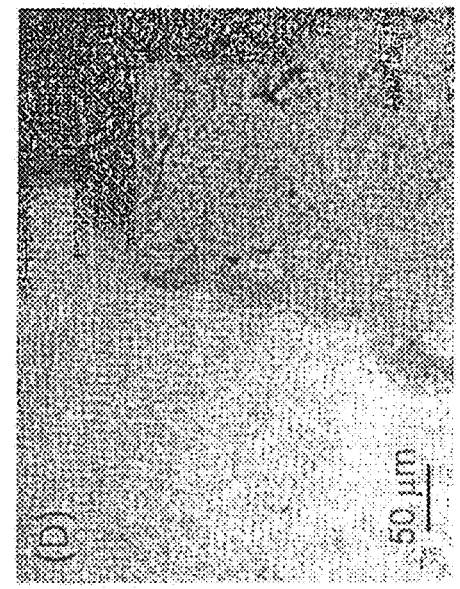
Figure 9:
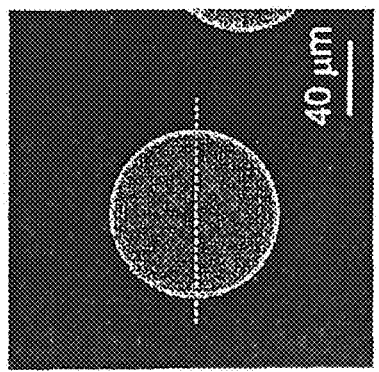

Dispersion liquid for a PLLA-4PEG film was prepared in the same manner as in Example 4 except that a 1.5 mass % PMMA acetone solution was applied on a PDMS stamper by spin coating (1,000 rpm, 20 seconds). The evaluation results are shown in FIG. 9 and Table 1. This polymer film agglomerate exhibited self-supportability at the gas-liquid interface (FIG. 9(C)), and the polymer films were overlapped with each other and existed as a single film (FIG. 9(D)). It was observed that on the skin model, the agglomerate was coated following the irregularities of the skin model (FIG. 9(E)).

Comparative Example 1 (Phase Separation Method)

A dichloromethane solution of 3.0 mass % PS/PVP=1/3 (mass ratio) was formed as a film by gravure method onto a PET film having been formed with 2 mass % PVA film thereon. The formed PS/PVP phase separation film was immersed in purified water to dissolve the PVA film and PVP. PVA and PVP were removed by centrifugal separation (4,000 rpm, 30 min, 3 times) to obtain dispersion liquid for a PS film. The evaluation results are shown in FIG. 10 and Table 2. This polymer film agglomerate did not exhibit self-supportability at the gas-liquid interface, and it was disintegrated.

Comparative Example 2 (Phase Separation Method)

Dispersion liquid for a PS film was prepared in the same manner as in Example 1 except that a dichloromethane solution of 2.0 mass % PS/PVP=1/4 (mass ratio) was used. The evaluation results are shown in FIG. 11 and Table 2. This polymer film agglomerate did not exhibit self-supportability at the gas-liquid interface, and it was disintegrated.

Comparative Example 3 (Phase Separation Method)

Dispersion liquid for a PS film was prepared in the same manner as in Example 1 except that a dichloromethane solution of 1.0 mass % PS/PVP=1/4 (mass ratio) was used. The evaluation results are shown in FIG. 12 and Table 2. This polymer film agglomerate did not exhibit self-supportability at the gas-liquid interface, and it was disintegrated.

Comparative Example 4 (Phase Separation Method)

An acetone solution of 2.0 mass % of PDLLA/PVP-PVAc=1/9 (mass ratio) was formed as a film by gravure method onto a PET film having been formed with 2.0 mass % PVA film thereon. The formed PDLLA/PVP-PVAc phase separation film was immersed in purified water to dissolve the PVA film and PVP-PVAc. PVA and PVP-PVAc were removed by centrifugal separation (4,000 rpm, 30 min, 3 times) using a centrifugal separator to obtain dispersion liquid for a PDLLA film. The evaluation results are shown in FIG. 13 and Table 2. This polymer film agglomerate did not exhibit self-supportability at the gas-liquid interface, and it was disintegrated.

Comparative Example 5 (Micro Contact Printing Method)

Dispersion liquid for a PDLLA film was prepared in the same manner as in Example 5 except that 1.5 mass % PDLLA ethyl acetate solution was applied on the PDMS stamper by spin coating (3,000 rpm, 20 seconds). The evaluation results are shown in FIG. 14 and Table 2. This polymer film agglomerate did not exhibit self-supportability at the gas-liquid interface, and it was disintegrated.

Comparative Example 6 (Spin Coating Method)

An ethyl acetate solution of 0.7 mass % of PDLLA was formed as a film by spin coating onto a silicon substrate having been formed with 2.0 mass % PVA film thereon. The formed PDLLA film was immersed in purified water to dissolve the PVA film to obtain a PDLLA film (5×5 mm$^2$) with a film thickness of 30 nm. Evaluation results are shown in FIG. 15 and Table 2. Although this polymer film was coated following the irregularities on the skin model (FIG. 15), it was peeled off from the skin model with a tape with adhesive strength of 0.22 N/cm, and it was weaker in adherence as compared with the polymer film agglomerates shown in Examples 1 to 3. Further, it could not be handled as a dispersion liquid.

Comparative Example 7 (Spin Coating Method)

An ethyl acetate solution of 7.5 mass % of PDLLA was formed as a film by spin coating onto a silicon substrate having been formed with 2.0 mass % PVA film thereon. The formed PDLLA film was immersed in purified water to dissolve the PVA film to obtain a PDLLA film (5×5 mm$^2$) with a film thickness of 30 nm. Evaluation results are shown in FIG. 16 and Table 2. This polymer film did not follow the irregularities on the skin model (FIG. 16) and was peeled off from the skin model with a tape with adhesive strength of 0.22 N/cm, and it was weaker in adherence as compared with the polymer film agglomerates shown in Examples 1 to 3. Further, it could not be handled as a dispersion liquid.

TABLE 1

|  | Example 1 | Example 2 | Example 3 | Example 4 | Example 5 | Example 6 | Example 7 |
| --- | --- | --- | --- | --- | --- | --- | --- |
| Polymer 1 | PDLLA | PDLLA | PDLLA | PDLLA | PLLA-4PEG | PLLA-4PEG | PMMA |
| Polymer 2 | PS | PS | PS | — | — | PVP | — |
| Mixing Ratio (Polymer 1:Polymer 2) (mass ratio) | 1:4 | 1:4 | 1:4 | — | — | 1:4 | — |
| Total polymer concentration (mass %) | 2.0 | 2.5 | 3.0 | 1.3 | 2.0 | 2.0 | 1.5 |
| Solvent | ethyl acetate | ethyl acetate | ethyl acetate | acetone | ethyl formate | dichloromethane | acetone |
| Film forming method | phase separation method | phase separation method | phase separation method | micro contact printing method | micro contact printing method | phase separation method | micro contact printing method |

TABLE 1-continued

|  | Example 1 | Example 2 | Example 3 | Example 4 | Example 5 | Example 6 | Example 7 |
|---|---|---|---|---|---|---|---|
| Shape | approximately circular shape/ approximately elliptical shape | approximately circular shape/ approximately elliptical shape | approximately circular shape/ approximately elliptical shape | approximately circular shape | approximately circular shape | approximately circular shape/ approximately elliptical shape | approximately circular shape |
| Average value L of distance 1 × 2 (μm) | 10 | 25 | 27 | 91 | 57 | 0.26 | 91 |
| Average value L of distance 1 (μm) | 5 | 13 | 14 | 46 | 29 | 0.13 | 46 |
| Average film thickness $T_0$ (nm) | 30 | 76 | 158 | 110 | 126 | 38 | 69 |
| Average film thickness $T_1$ (nm) | 32 | 84 | 166 | 114 | 178 | 32 | 77 |
| Average film thickness $T_2$ (nm) | 27 | 68 | 143 | 107 | 76 | 43 | 60 |
| Young's modulus E (GPa) | 0.89 | 1.4 | 2.2 | 1.7 | 0.065 | 0.065 | 3.1 |
| $0.346E \times 10^{-9} - 1.499$ | −1.19 | −1.01 | −0.74 | −0.91 | −1.48 | −1.48 | −0.43 |
| Deviation Δ | −0.19 | −0.24 | −0.16 | −0.067 | −1.33 | 0.26 | −0.28 |
| $-0.073E \times 10^{-9} + 0.316$ | 0.25 | 0.21 | 0.16 | 0.19 | 0.31 | 0.31 | 0.09 |
| Self supportability | A | A | A | A | A | A | A |
| Coatability | A | A | A | — | A | — | A |
| Adherence (4.0 N/cm) | 0 | 0 | 5 | — | — | — | — |
| Adherence (0.22 N/cm) | 0 | 0 | 0 | — | — | — | — |

TABLE 2

|  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| Polymer 1 | PS | PS | PS | PDLLA | PDLLA | PDLLA | PDLLA |
| Polymer 2 | PVP | PVP | PVP | PVPPVAc | — | — | — |
| Mixing Ratio (Polymer 1:Polymer 2) (mass ratio) | 1:3 | 1:4 | 1:4 | 1:9 | — | — | — |
| Total polymer concentration (mass %) | 3.0 | 2.0 | 1.0 | 2.0 | 1.5 | 0.7 | 7.5 |
| Solvent | dichloromethane | dichloromethane | dichloromethane | acetone | ethyl acetate | ethyl acetate | ethyl acetate |
| Film forming method | phase separation method | phase separation method | phase separation method | phase separation method | micro contact printing | Spin coating method | Spin coating method |
| Shape | approximately circular shape/ approximately elliptical shape | approximately circular shape/ approximately elliptical shape | approximately circular shape/ approximately elliptical shape | approximately circular shape/ approximately elliptical shape | approximately circular shape | Continuous film (5 mm square) | Continuous film (5 mm square) |
| Average value L of distance 1 × 2 (μm) | 3.7 | 1.9 | 0.53 | 0.57 | 93 | — | — |
| Average value L of distance 1 (μm) | 1.9 | 1.0 | 0.27 | 0.29 | 47 | — | — |
| Average film thickness $T_0$ (nm) | 458 | 218 | 63 | 138 | 93 | 30 | 1200 |
| Average film thickness $T_1$ (nm) | 395 | 196 | 56 | 125 | 123 | — | — |
| Average film thickness $T_2$ (nm) | 474 | 238 | 70 | 150 | 62 | — | — |
| Young's modulus E (GPa) | 3.5 | 3.5 | 3.2 | 2.0 | 1.5 | — | — |
| $0.346E \times 10^{-9} - 1.499$ | −0.29 | −0.29 | −0.39 | −0.81 | −0.98 | — | — |
| Deviation Δ | 0.17 | 0.18 | 0.20 | 0.17 | −0.98 | — | — |
| $-0.073E \times 10^{-9} + 0.316$ | 0.06 | 0.06 | 0.08 | 0.17 | 0.21 | — | — |
| Self supportability | B | B | B | B | B | — | — |
| Coatability | — | — | — | — | — | A | B |
| Adherence (4.0 N/cm) | — | — | — | — | — | 5 | 5 |
| Adherence (0.22 N/cm) | — | — | — | — | — | 5 | 5 |

INDUSTRIAL APPLICABILITY

The polymer film can accumulate by overlapping with each other while exhibiting high followability to adherends, and can form a film exhibiting high adherence and stability. For example, it is optimum for hemostasis at surgical operation, wound-dressing materials, adhesion-preventing materials, cosmetic materials, percutaneous absorbing materials and the like. Further, it can also be used as a coating agent or the like by dispersing it in an aqueous solvent.

The invention claimed is:

1. A polymer film having an average film thickness $T_0$ along a straight line D passing through a center of gravity of a two-dimensional projection such that an area of the polymer film is maximized, satisfies equation (a), an average value L of distances l from the center of gravity to edges in straight lines D passing through a center of gravity satisfies equation (b), a Young's modulus E satisfies equation (c), and a thickness deviation Δ defined by equation (d) satisfies equation (e):

$$10 \text{ nm} \leq T_0 \leq 1000 \text{ nm} \quad (a)$$

$$0.1 \text{ μm} \leq L \leq 500 \text{ μm} \quad (b)$$

$$0.01 \text{ GPa} \leq E \leq 4.3 \text{ GPa} \quad (c)$$

$$\Delta = 1 - T_1/T_2 \quad (d)$$

$$0.346E \times 10^{-9} - 1.499 < \Delta < -0.073E \times 10^{-9} + 0.316 \quad (e)$$

where $T_1$ and $T_2$ represent, in the straight lines D passing through the center of gravity of the two-dimensional projection such that the area of the polymer film is maximized, $T_1$: an average film thickness of a region from ½ to 1 of the distance l from the center of gravity to the edge, and $T_2$: an average film thickness of a region from the center of gravity to ¼, and the straight line D passing through the center of gravity of the two-dimensional projection means $D_1$ to $D_4$:

(1) a minor axis passing through the center of gravity: $D_1$, (2) a major axis passing through the center of gravity: $D_2$, (3) straight lines passing through the center of gravity and bisecting a wide angle and a narrow angle formed by the minor axis and the major axis respectively: $D_3$, $D_4$, when the minor axis and the major axis are the same or there are a plurality, two lines having the smallest difference between the wide angle and the narrow angle formed by the minor axis and the major axis are selected, and average film thickness means an average value calculated using the four straight lines $D_1$ to $D_4$;

wherein a polymer constituting the polymer film is a homopolymer selected from the group consisting of a polyester-based resin, a polyether-based resin, a polymethacrylate-based resin, a polysaccharide and a polysaccharide ester, and/or a copolymer containing at least one polymer selected from the group consisting of a polyester-based resin, a polyether-based resin, a polymethacrylate-based resin, a polysaccharide and a polysaccharide ester.

2. The polymer film according to claim 1, wherein the polymer film has at least one shape selected from the group consisting of a circle, an ellipse, an approximately circular shape, an approximately elliptical shape, an approximately polygonal shape and a ribbon shape.

3. A dispersion liquid in which the polymer film according to claim 1 is dispersed in a solution.

4. A polymer film agglomerate comprising the polymer film according to claim 1.

5. A dispersion liquid in which the polymer film according to claim 2 is dispersed in a solution.

6. A polymer film agglomerate using comprising the polymer film according to claim 2.

* * * * *

UNITED STATES PATENT AND TRADEMARK OFFICE
CERTIFICATE OF CORRECTION

Page 1 of 1

PATENT NO. : 10,563,025 B2
APPLICATION NO. : 15/572210
DATED : February 18, 2020
INVENTOR(S) : Hochi et al.

It is certified that error appears in the above-identified patent and that said Letters Patent is hereby corrected as shown below:

In the Specification

In Column 2
Line 34, please change "horacic" to -- thoracic --.

In Column 7
Line 28, please change "$10^{-9}$ 1.352" to -- $10^{-9}$ - 1.352 --.

In Column 12
Line 10, please change "BASE" to -- BASF --.

In Column 12
Line 14, please change "foray" to -- Toray --.

In Column 14
Line 24, please change "1-$^{v^2}$PDMS" to -- 1-$^v$PDMS$^2$ --.

Signed and Sealed this
Sixteenth Day of June, 2020

Andrei Iancu
*Director of the United States Patent and Trademark Office*